(12) United States Patent
Keller et al.

(10) Patent No.: US 12,220,114 B2
(45) Date of Patent: *Feb. 11, 2025

(54) BIOPSY DEVICE WITH APPLIED IMAGING

(71) Applicant: Devicor Medical Products, Inc., Cincinnati, OH (US)

(72) Inventors: Bryan R. Keller, Loveland, OH (US); Patrick A. Mescher, Bellbrook, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/852,633

(22) Filed: Jun. 29, 2022

(65) Prior Publication Data
US 2022/0323052 A1     Oct. 13, 2022

Related U.S. Application Data

(63) Continuation of application No. 16/208,814, filed on Dec. 4, 2018, now Pat. No. 11,399,812.
(Continued)

(51) Int. Cl.
*A61B 10/02* (2006.01)
*A61B 10/00* (2006.01)
(Continued)

(52) U.S. Cl.
CPC ...... *A61B 10/0275* (2013.01); *A61B 10/0096* (2013.01); *A61B 90/39* (2016.02);
(Continued)

(58) Field of Classification Search
CPC . G06N 20/20; G06N 5/01; A61B 5/16; A61B 5/163; A61B 5/168; A61B 5/0077; A61B 2503/06; G06F 18/2148
See application file for complete search history.

(56) References Cited

U.S. PATENT DOCUMENTS

| 5,526,822 A | 6/1996 | Burbank et al. |
| 5,928,164 A | 7/1999 | Burbank et al. |

(Continued)

FOREIGN PATENT DOCUMENTS

| CN | 103501708 A | 1/2014 |
| JP | 2008-139322 A | 6/2008 |

(Continued)

OTHER PUBLICATIONS

Hahn, M., et al., "Diagnostic Primer: Vacuum-Assisted Breast Biopsy with Mammotome®," Devicor Medical Germany GmbH, Nov. 11, 2012, Germany, Springer Medizin Verlag, copyright 2013, 130 pgs.

(Continued)

*Primary Examiner* — Rene T Towa
(74) *Attorney, Agent, or Firm* — Frost Brown Todd LLP

(57) ABSTRACT

A biopsy device includes a body, a needle, a tissue sample holder and a sensor. The needle extends from the body. The tissue sample holder is in communication with the needle to receive one or more tissue samples within a sample chamber defined by the tissue sample holder. The tissue sample holder includes a receiving cavity. The sensor is configured to detect x-rays. The receiving cavity is sized and shaped to receive the sensor such that the sensor is removably positioned within the tissue sample holder.

20 Claims, 21 Drawing Sheets

Related U.S. Application Data

(60) Provisional application No. 62/594,796, filed on Dec. 5, 2017.

(51) Int. Cl.
*A61B 90/00* (2016.01)
*A61B 10/04* (2006.01)

(52) U.S. Cl.
CPC ... *A61B 2010/0208* (2013.01); *A61B 10/0283* (2013.01); *A61B 2010/045* (2013.01); *A61B 2090/376* (2016.02); *A61B 2090/3937* (2016.02)

(56) References Cited

U.S. PATENT DOCUMENTS

| | | | |
|---|---|---|---|
| 6,017,316 A | 1/2000 | Ritchart et al. | |
| 6,086,544 A | 4/2000 | Hibner et al. | |
| 6,162,187 A | 12/2000 | Buzzard et al. | |
| 6,432,065 B1 | 8/2002 | Burdorff et al. | |
| 6,626,849 B2 | 9/2003 | Huitema et al. | |
| 6,752,768 B2 | 6/2004 | Burdorff et al. | |
| 7,442,171 B2 | 10/2008 | Stephens et al. | |
| 7,648,466 B2 | 1/2010 | Stephens et al. | |
| 7,837,632 B2 | 11/2010 | Stephens et al. | |
| 7,854,706 B2 | 12/2010 | Hibner | |
| 7,914,464 B2 | 3/2011 | Burdorff et al. | |
| 7,918,803 B2 | 4/2011 | Ritchart et al. | |
| 7,918,804 B2 | 4/2011 | Monson et al. | |
| 7,938,786 B2 | 5/2011 | Ritchie et al. | |
| 8,083,687 B2 | 12/2011 | Parihar | |
| 8,118,755 B2 | 2/2012 | Hibner et al. | |
| 8,206,315 B2 | 6/2012 | Mark et al. | |
| 8,206,316 B2 | 6/2012 | Hibner et al. | |
| 8,241,226 B2 | 8/2012 | Hibner et al. | |
| 8,454,531 B2 | 6/2013 | Speeg et al. | |
| 8,622,924 B2 | 1/2014 | Speeg et al. | |
| 8,702,623 B2 | 4/2014 | Parihar et al. | |
| 8,764,680 B2 | 7/2014 | Rhad et al. | |
| 8,801,742 B2 | 8/2014 | Rhad et al. | |
| 8,858,465 B2 | 10/2014 | Fiebig | |
| 8,938,285 B2 | 1/2015 | Fiebig et al. | |
| 9,095,326 B2 | 8/2015 | Ritchie et al. | |
| 9,107,651 B2 | 8/2015 | Satoh et al. | |
| 9,326,755 B2 | 5/2016 | Fiebig et al. | |
| 9,345,457 B2 | 5/2016 | Speeg et al. | |
| 9,724,076 B2 | 8/2017 | Fiebig et al. | |
| 9,867,599 B2 | 1/2018 | Hendriks et al. | |
| 9,955,955 B2 | 5/2018 | Fiebig et al. | |
| 10,905,404 B2 | 2/2021 | Choung et al. | |
| 2003/0202630 A1* | 10/2003 | Chen | A61B 1/042 378/62 |
| 2005/0287523 A1 | 12/2005 | Letant et al. | |
| 2006/0074345 A1 | 4/2006 | Hibner | |
| 2006/0134600 A1 | 6/2006 | Fuhr et al. | |
| 2008/0045833 A1* | 2/2008 | Defreitas | A61B 10/0041 600/429 |
| 2008/0156092 A1* | 7/2008 | Boiarski | A61F 5/4404 73/304 R |
| 2009/0131821 A1 | 5/2009 | Speeg et al. | |
| 2010/0152610 A1 | 6/2010 | Parihar et al. | |
| 2010/0160819 A1 | 6/2010 | Parihar et al. | |
| 2012/0283563 A1* | 11/2012 | Moore | A61B 8/463 600/437 |
| 2013/0324882 A1 | 12/2013 | Mescher | |
| 2014/0039343 A1 | 2/2014 | Mescher et al. | |
| 2016/0151055 A1 | 6/2016 | LeBlond et al. | |
| 2017/0311935 A1* | 11/2017 | Choung | A61B 10/0275 |
| 2018/0049728 A1* | 2/2018 | Berlin | A61B 10/0283 |

FOREIGN PATENT DOCUMENTS

| | | |
|---|---|---|
| JP | 2013-535014 A | 9/2013 |
| WO | 2007/095330 A2 | 8/2007 |
| WO | 2018/039253 A1 | 3/2018 |

OTHER PUBLICATIONS

Chinese Office Action dated May 26, 2023 for Application No. 201880085990.X, 7 pages.
European Communication dated Mar. 23, 2021 for Application No. 18829577.8, 11 pages.
European Communication dated Aug. 31, 2021 for Application No. 18829577.8, 6 pages.
European Communication dated Dec. 19, 2023 for Application No. 23204092.3, 10 pages.
Japanese Office Action dated May 15, 2024 for Application No. 2023-132574, 9 pages.
Korean Office Action dated Oct. 30, 2024 for Application No. 10-2020-7018460, 6 pages.
International Search Report and Written Opinion dated Apr. 26, 2019 for Application No. PCT/US2018/063742, 15 pgs.

\* cited by examiner

BIOPSY DEVICE WITH APPLIED IMAGING

PRIORITY

This application is a continuation of U.S. Ser. No. 16/208,814, filed on Dec. 4, 2018, published as U.S. Pub. No. 2019/0167238 on Jun. 6, 2019, which claims priority to U.S. Provisional Patent App. No. 62/594,796 entitled "Biopsy Device with Applied Imaging," filed on Dec. 5, 2017, the disclosures of which are incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 7,442,171, entitled "Remote Thumbwheel for a Surgical Biopsy Device," issued Oct. 8, 2008; U.S. Pat. No. 7,854,706, entitled "Clutch and Valving System for Tetherless Biopsy Device," issued Dec. 1, 2010; U.S. Pat. No. 7,938,786, entitled "Vacuum Timing Algorithm for Biopsy Device," issued May 10, 2011; and U.S. Pat. No. 8,118,755, entitled "Biopsy Sample Storage," issued Feb. 21, 2012. The disclosure of each of the above-cited U.S. Patents is incorporated by reference herein.

After extracting a biopsy specimen from a patient using one of the above disclosed exemplary biopsy devices or biopsy system components, an operator may desire to examine the tissue specimen through certain imaging modalities. The operator may be limited in the promptness of examining the sample under such conditions as the time required to extract the tissue sample from the biopsy device, position the sample into an examination container, and subsequently insert the examination container into an imaging system to produce images of the specimen for analysis is extensive.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
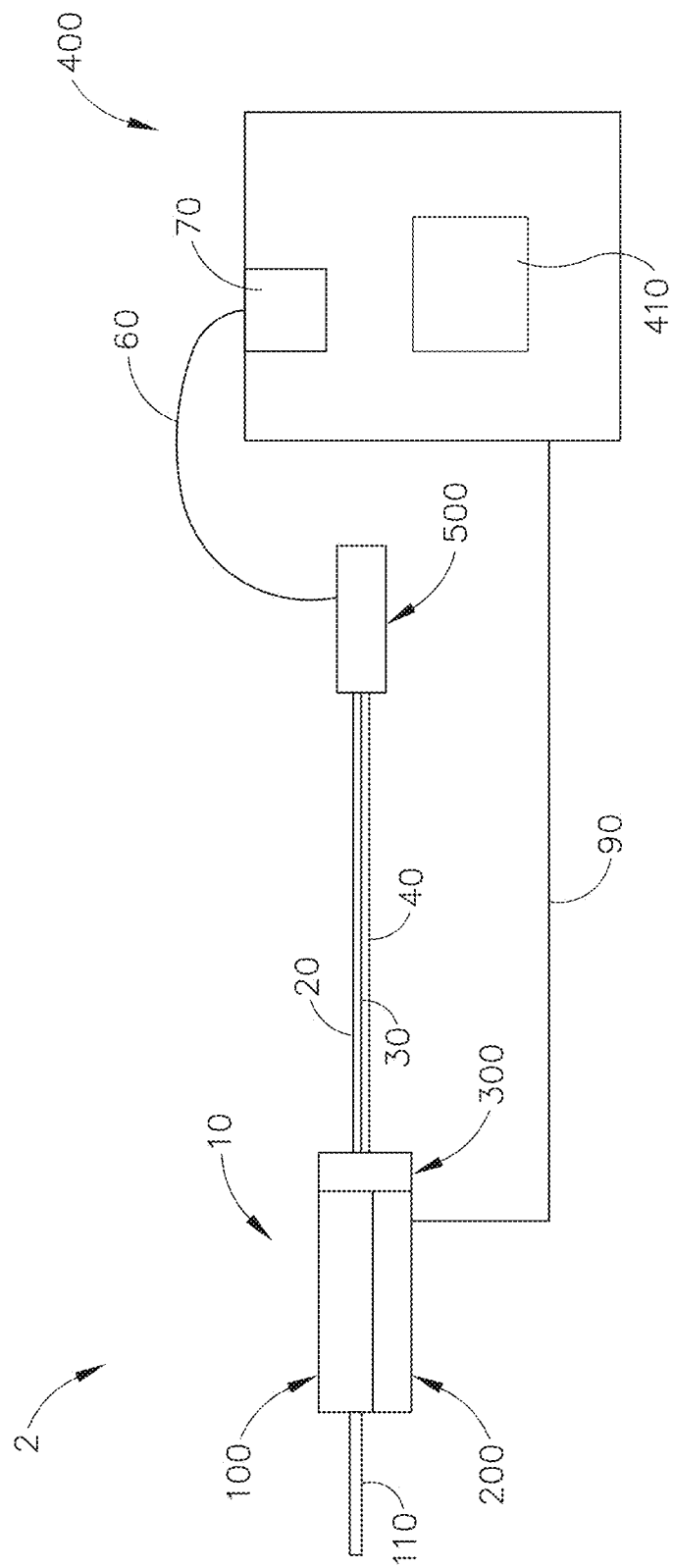
FIG. 1 depicts a schematic view of an exemplary biopsy system including a biopsy device and a vacuum control module.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. OVERVIEW OF EXEMPLARY BIOPSY SYSTEM

Figure 2:
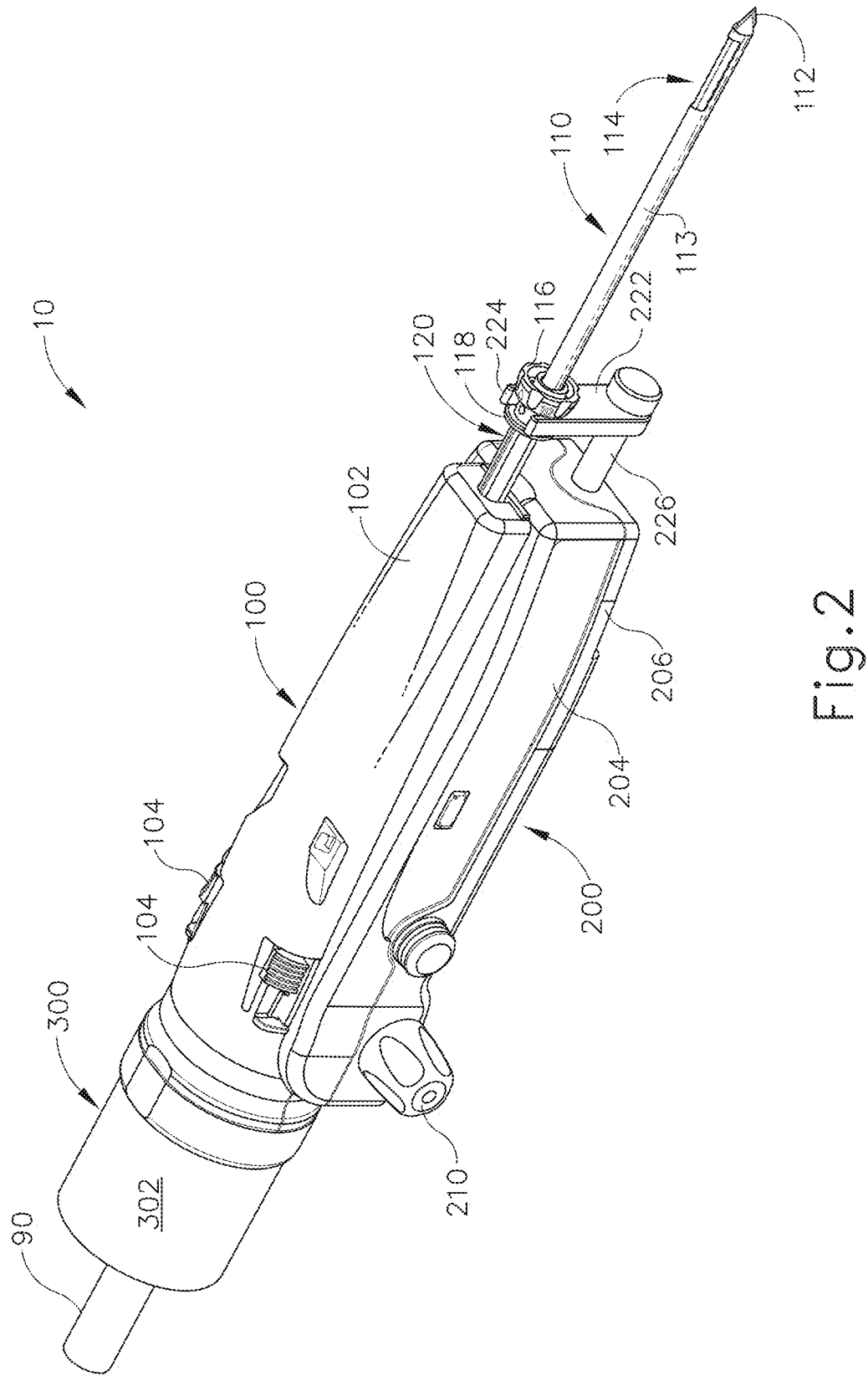
FIG. 2 depicts a perspective view of an exemplary biopsy device of the biopsy system of FIG. 1, including an exemplary probe coupled with an exemplary holster.
Figure 3:
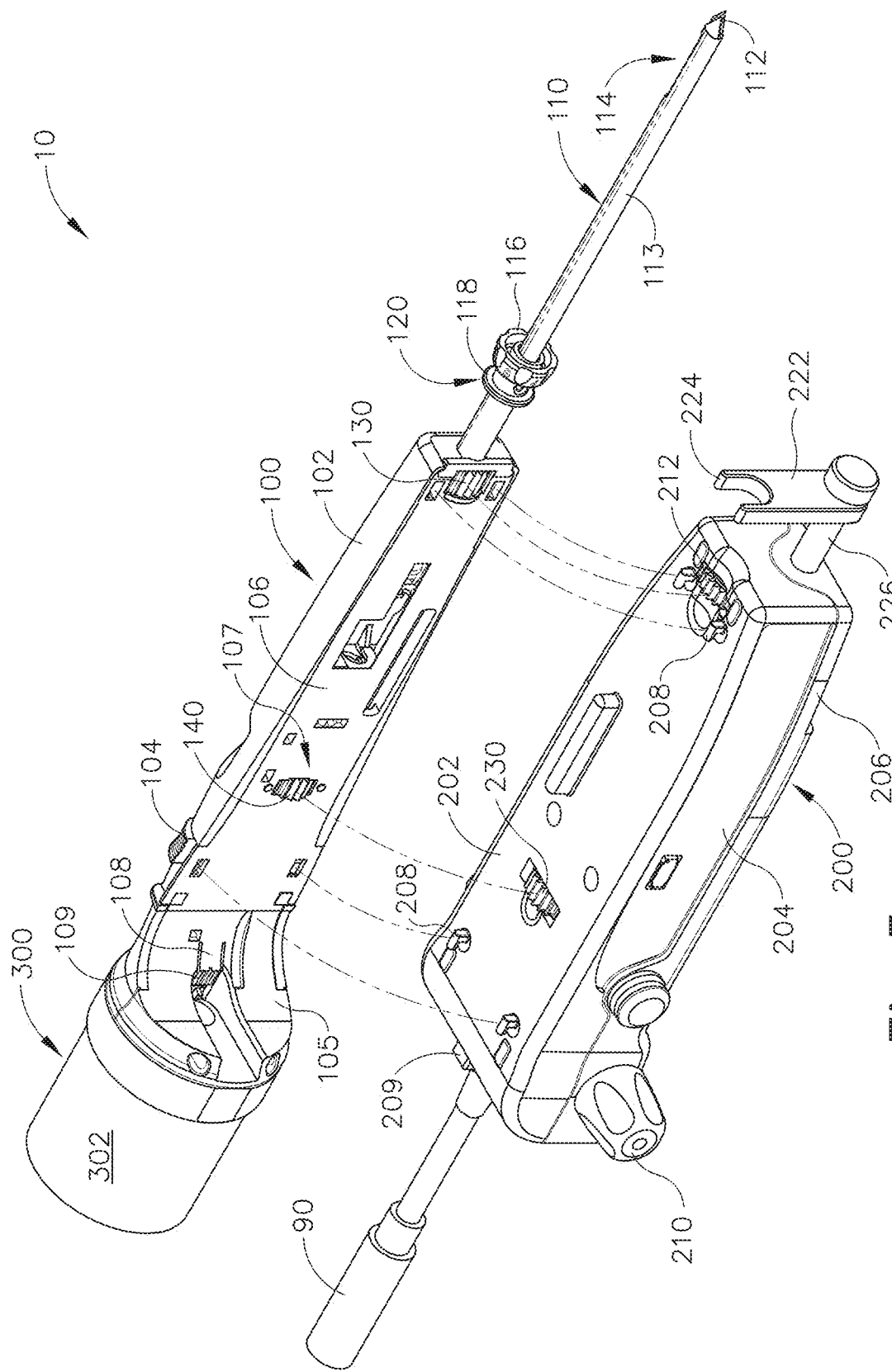
FIG. 3 depicts a perspective view of the biopsy device of FIG. 2, with the probe decoupled from the holster.

FIG. 1 depicts an exemplary biopsy system (2) comprising a biopsy device (10) and a vacuum control module (400). Biopsy device (10) of this example comprises a probe (100) and a holster (200), as shown in FIGS. 2-3. A needle (110) extends distally from probe (100), and is inserted into a patient's tissue to obtain tissue samples. These tissue samples are deposited in a tissue sample holder (300) at the proximal end of probe (100), as will also be described in greater detail below. It should also be understood that the use of the term "holster" herein should not be read as requiring any portion of probe (100) to be inserted into any portion of holster (200). In the present example, holster (200) includes a set of prongs (208) that are received by the chassis (106) of probe (100) to releasably secure probe (100) to holster (200). In particular, probe (100) is first positioned on top of holster (200), just proximal to its final position relative to holster (200); then probe (100) is slid distally to fully engage prongs (208). Probe (100) also includes a set of resilient tabs (104) that may be pressed inwardly to disengage prongs (208), such that a user may simultaneously depress both tabs (104) then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition, or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a hall effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Of course, such sensors and features may be varied or omitted as desired.

Biopsy device (10) of the present example is configured to mount to a table or fixture, and be used under stereotactic guidance. Of course, biopsy device (10) may instead be used under ultrasound guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In some settings, the user may capture a plurality of tissue samples with just a single insertion of needle (110) into the patient's breast. Such tissue samples may be pneumatically deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

II. EXEMPLARY HOLSTER

As shown in FIG. 3, holster (200) of the present example includes a top housing cover (202), side panels (204), and a housing base (206), which are fixedly secured together. Gears (212, 230) are exposed through top housing cover (202), and mesh with gears (130, 140) of probe (100) when probe (100) and holster (200) are coupled together. In particular, gears (230, 140) drive the actuation assembly of a cutter (150) within needle (110); while gears (212, 130) are employed to rotate needle (110). Gear (240) is located at the proximal end of holster (200) and meshes with gear (182) of probe (100) to rotate a rotatable member (310) of tissue sample holder (300).

As noted above, rotation of gear (212) provides rotation of needle (110) relative to probe (100). In the present example, gear (212) is rotated by rotating knob (210). In particular, knob (210) is coupled with gear (212) by a series of gears (not shown) and shafts (not shown), such that rotation of knob (210) rotates gear (212). A second knob (210) extends from the other side of holster (200). By way of example only, such a needle rotation mechanism may be constructed in accordance with the teachings of U.S. Pub. No. 2008/0214955, the disclosure of which is incorporated by reference herein. As another merely illustrative example, a needle rotation mechanism may be constructed in accordance with the teachings of U.S. Pub. No. 2010/0160819, the disclosure of which is incorporated by reference herein. In some other versions, needle (110) is rotated by a motor. In still other versions, needle (110) is simply rotated by rotating thumbwheel (116). Various other suitable ways in which rotation of needle (110) may be provided will be apparent to those of ordinary skill in the art in view of the teachings herein. It should also be understood that some versions may provide no rotation of needle (110).

Holster (200) also includes a firing rod (226) and fork (222), which couple with needle (110) and fire needle (110) distally. By way of example only, such firing may be useful in instances where biopsy device (10) is mounted to a stereotactic table fixture or other fixture, with tip (112) adjacent to a patient's breast, such that the needle firing mechanism may be activated to drive needle (110) into the patient's breast. The needle firing mechanism may be configured to drive needle (110) along any suitable range of motion, to drive tip (112) to any suitable distance relative to fixed components of probe (100).

In the present example, the needle firing mechanism is coupled with needle (110) via a firing rod (226) and a firing fork (222). Firing rod (226) and firing fork (222) are unitarily secured together. Firing fork (222) includes a pair of prongs (224) that receive hub member (120) of needle (110) therebetween. Prongs (224) are positioned between annular flange (118) and thumbwheel (116), such that needle (110) will translate unitarily with firing rod (226) and fork (222). Prongs (224) nevertheless removably receive hub member (120), such that fork (222) may be readily secured to hub member (120) when probe (100) is coupled with holster (200); and such that hub member (120) may be readily removed from fork (222) when probe (100) is decoupled from holster (200). Prongs (224) are also configured to permit hub member (120) to rotate between prongs (224). Other suitable components, configurations, and relationships will be apparent to those of ordinary skill in the art in view of the teachings herein. The internal components of the needle firing mechanism of the present example are configured and arranged as described in U.S. Pat. No. 8,858,465, entitled "Biopsy Device with Motorized Needle Firing," issued Oct. 14, 2014, the disclosure of which is incorporated by reference herein.

Holster (200) includes motors (not shown) to drive gears (230, 240) to thereby rotate and translate cutter (150) and rotate rotatable member (310) of tissue sample holder (300). Holster (200) also includes a motor (not shown) that is operable to drive firing rod (226), to thereby arm and fire needle (110). All motors referred to herein are contained within holster (200) in the present example and receive power from vacuum control module (400) via cable (90). In addition, data may be communicated between vacuum control module (400) and holster (200) via cable (90). As will be described in greater detail below, such data may be used by control module (400) to display certain graphical user interface screens on a touchscreen (410) integrated into control module (400). In some other versions, one or more motors are powered by one or more batteries located within holster (200) and/or probe (100). It should therefore be understood that, as with other components described herein, cable (90) is merely optional. As yet another merely illustrative variation, motors may be powered pneumatically, such that cable (90) may be substituted with a conduit communicating a pressurized fluid medium to holster (200). As still other merely illustrative variation, cable (90) may include one or more rotary drive cables that are driven by motors that are located external to holster (200). It should also be understood that two or three of the motors may be combined as a single motor. Other suitable ways in which various the motors may be driven will be apparent to those of ordinary skill in the art in view of the teachings herein.

III. EXEMPLARY PROBE

Probe (100) of the present example includes a needle (110) extending distally from probe (100) that is inserted into a patient's tissue to obtain tissue samples. These tissue samples are deposited in a tissue sample holder (300) at the proximal end of probe (100). As shown in FIG. 1, vacuum control module (400) is coupled with probe (100) via a valve assembly (500) and tubes (20, 30, 40, 60), which is operable to selectively provide vacuum, saline, atmospheric air, and venting to probe (100). The internal components of the valve assembly of the present example are configured and arranged as described in U.S. Pub. No. 2013/0218047, entitled "Biopsy Device Valve Assembly," published Aug. 22, 2013, the disclosure of which is incorporated by reference herein.

As shown in FIGS. 1-6, probe (100) also includes a chassis (106) and a top housing (102), which are fixedly secured together. As best seen in FIG. 3, a gear (140) is exposed through an opening (107) in chassis (106), and is operable to drive cutter actuation mechanism in probe (100). As also seen in FIG. 3, another gear (130) is exposed through chassis (106), and is operable to rotate needle (110) as will be described in greater detail below. Gear (140) of probe (100) meshes with exposed gear (230) of holster (200) when probe (100) and holster (200) are coupled together.

Similarly, gear (130) of probe (100) meshes with exposed gear (212) of holster (200) when probe (100) and holster (200) are coupled together.

A. Exemplary Needle Assembly

Needle (110) of the present example comprises a cannula (113) having a tissue piercing tip (112), a lateral aperture (114) located proximal to tip (112), and a hub member (120). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Pat. No. 8,801,742, entitled "Needle Assembly and Blade Assembly for Biopsy Device," issued Aug. 12, 2014, the disclosure of which is incorporated by reference herein. As another merely illustrative example, tip (112) may be configured in accordance with at least some of the teachings in U.S. Pub. No. 2013/0150751, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (150) having a sharp distal edge (152) is located within needle (110). Cutter (150) is operable to rotate and translate relative to needle (110) and past lateral aperture (114) to sever a tissue sample from tissue protruding through lateral aperture (114). For instance, cutter (150) may be moved from an extended position to a retracted position, thereby "opening" lateral aperture (114) to allow tissue to protrude therethrough; then from the retracted position back to the extended position to sever the protruding tissue. As will be described in greater detail below, needle (110) may be rotated to orient lateral aperture (114) at any desired angular position about the longitudinal axis of needle (110). Such rotation of needle (110) is facilitated in the present example by hub member (120), which is described in greater detail below.

Figure 6:
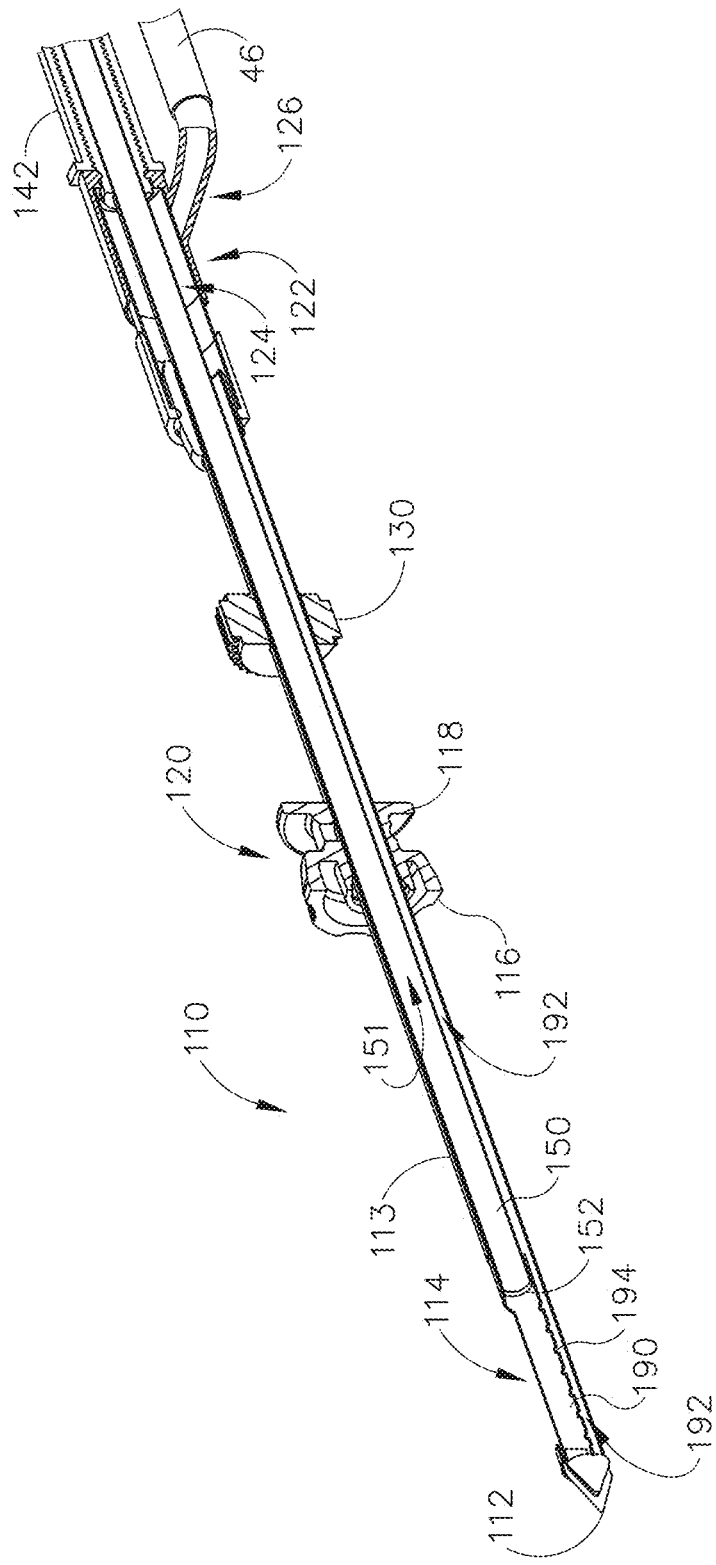
FIG. 6 depicts a cross-sectional view of a needle assembly of the probe of FIG. 4.

As best seen in FIG. 6, needle (110) also includes a longitudinal wall (190) extending proximally from the proximal portion of tip (112). While wall (190) does not extend along the full length of cannula (113) in this example, it should be understood that wall (190) may extend the full length of cannula (113) if desired. Wall (190) defines a distal portion of a second lumen (192) that is lateral to and parallel to cutter (150). Wall (190) proximally terminates at a longitudinal position that is just proximal to the location of distal cutting edge (152) of cutter (150) when cutter (150) is in a proximal-most position as shown in FIG. 6. The exterior of cutter (150) and the interior of cannula (113) together define the proximal portion of second lumen (192) in the length of needle (110) that is proximal to the proximal end of wall (190).

Wall (190) includes a plurality of openings (194) that provide fluid communication between second lumen (192) and the region within cannula (113) that is above wall (190) and below lateral aperture (114). This further provides fluid communication between second lumen (192) and the lumen (151) defined by the interior of cutter (150), as will be described in greater detail below. Openings (194) are arranged such that at least one opening (194) is located at a longitudinal position that is distal to the distal edge of lateral aperture (114). Thus, the lumen (151) of cutter (150) and second lumen (192) may remain in fluid communication even when cutter (150) is advanced to a position where the distal cutting edge of cutter (150) is located at a longitudinal position that is distal to the longitudinal position of the distal edge of lateral aperture (114). An example of such a configuration is disclosed in U.S. Pat. No. 7,918,803, entitled "Methods and Devices for Automated Biopsy and Collection of Soft Tissue," issued Apr. 5, 2011, the disclosure of which is incorporated by reference herein. Of course, as with any other component described herein, any other suitable configurations may be used.

A plurality of external openings (not shown) may also be formed in needle (110), and may be in fluid communication with second lumen (192). For instance, such external openings may be configured in accordance with the teachings of U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings in needle (110) are merely optional.

Hub member (120) of the present example is overmolded about needle (110), such that hub member (120) and needle (110) rotate and translate unitarily with each other. By way of example only, needle (110) may be formed of metal, and hub member (120) may be formed of a plastic material that is overmolded about needle (110) to unitarily secure and form hub member (120) to needle (110). Hub member (120) and needle (110) may alternatively be formed of any other suitable material(s), and may be secured together in any other suitable fashion. Hub member (120) includes an annular flange (118) and a thumbwheel (116). Gear (130) is slidably and coaxially disposed on a proximal portion (150) of hub member (120) and is keyed to hub member (120), such that rotation of gear (130) will rotate hub member (120) and needle (110); yet hub member (120) and needle (110) may translate relative to gear (130). Gear (130) is rotatably driven by gear (212). Alternatively, needle (110) may be rotated by rotating thumbwheel (116). Various other suitable ways in which manual rotation of needle (110) may be provided will be apparent to those of ordinary skill in the art in view of the teachings herein. It should also be understood that rotation of needle (110) may be automated in various ways, including but not limited to the various forms of automatic needle rotation described in various references that are cited herein.

As shown in FIGS. 4-7, a manifold (122) is attached, mounted, or otherwise secured to the proximal end of needle (110). Manifold (122) defines a hollow interior (124) and includes a port (126) in fluid communication with hollow interior (124). As best seen in FIG. 6, hollow interior (124) is also in fluid communication with second lumen (192) of needle (110). Port (126) is coupled with tube (46), such that manifold (122) provides fluid communication between second lumen (192) and tube (46). Manifold (122) also seals against the exterior of needle (110) such that manifold (122) provides a fluid tight coupling between second lumen (192) and tube (46) even if needle (110) is translated and/or rotated relative to manifold (122), such as during firing of needle (110) or re-orientation of needle (110), respectively.

Figure 4:
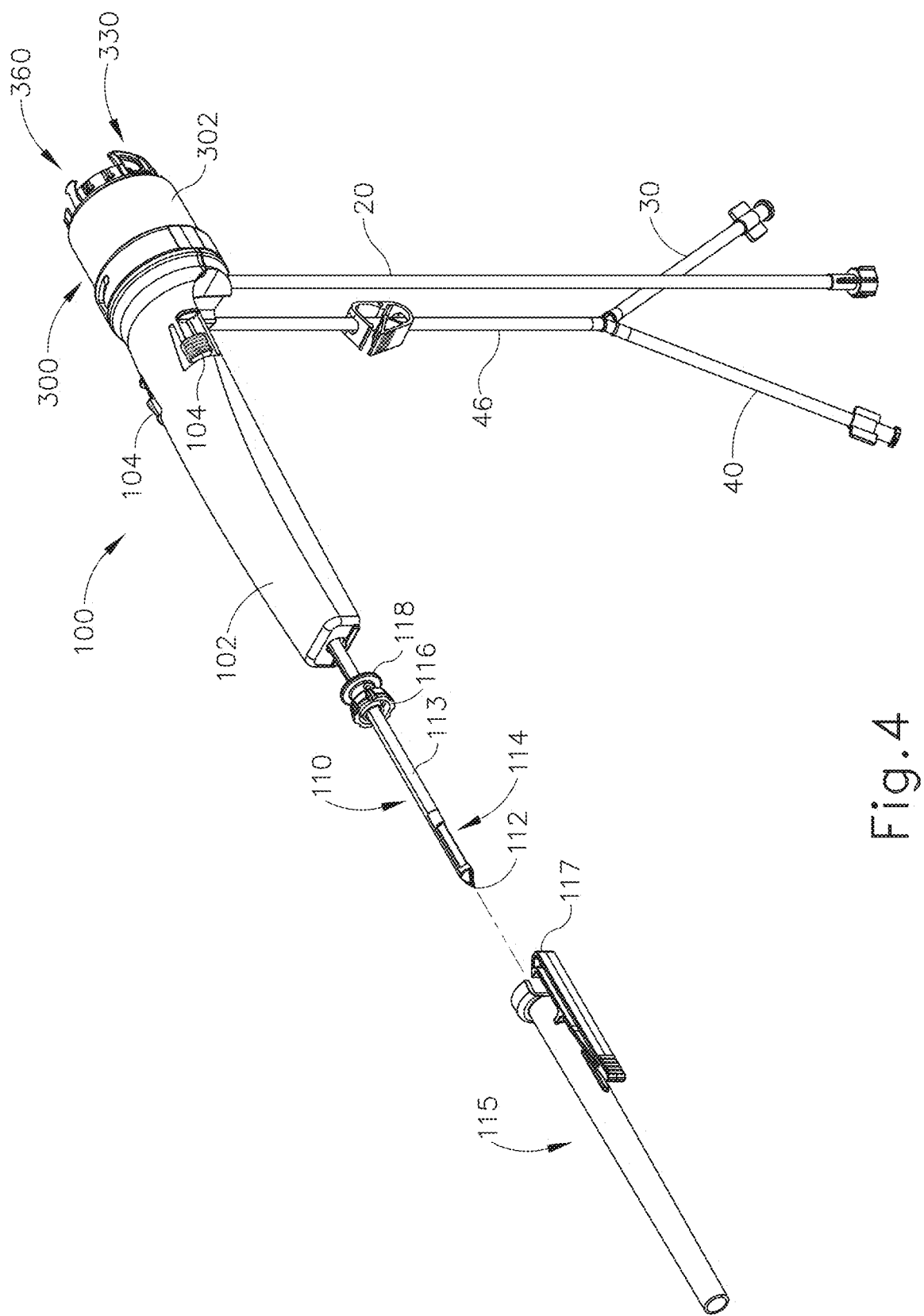
FIG. 4 depicts a perspective view of the probe of the biopsy device of FIG. 2.

As shown in FIG. 4, needle (110) may be provided with a removable cover (115). Cover (115) of this example includes a resiliently biased latch (117) that is configured to engage thumbwheel (116), to thereby removably secure cover (115) to needle (110). Cover (115) is configured to cover tip (112) when latch (117) is engaged with thumbwheel (116), such that cover (115) protects the user of biopsy device (10) from inadvertent contact with tip (112). Cover (115) may also include one or more wiper seals near the proximal end and/or distal end of cover (115), to seal against cannula (113). By way of example only, cover (115) may be configured in accordance with at least some of the teachings in U.S. Pub. No. 2013/0150751, the disclosure of which is incorporated by reference herein. Various other suitable configurations for cover (115) will be apparent to those of ordinary skill in the art in view of the teachings herein. Of course, cover (115) may simply be omitted if desired. It should also be understood that, as with other components described herein, needle (110) may be varied, modified, substituted, or supplemented in a variety of ways; and that needle (110) may have a variety of alternative features, components, configurations, and functionalities. For instance, needle (110) may be constructed in accordance with the teachings of U.S. Pub. No. 2008/0214955, the disclosure of which is incorporated by reference herein, and/or in accordance with the teachings of any other reference cited herein.

B. Exemplary Cutter Assembly

Figure 5:
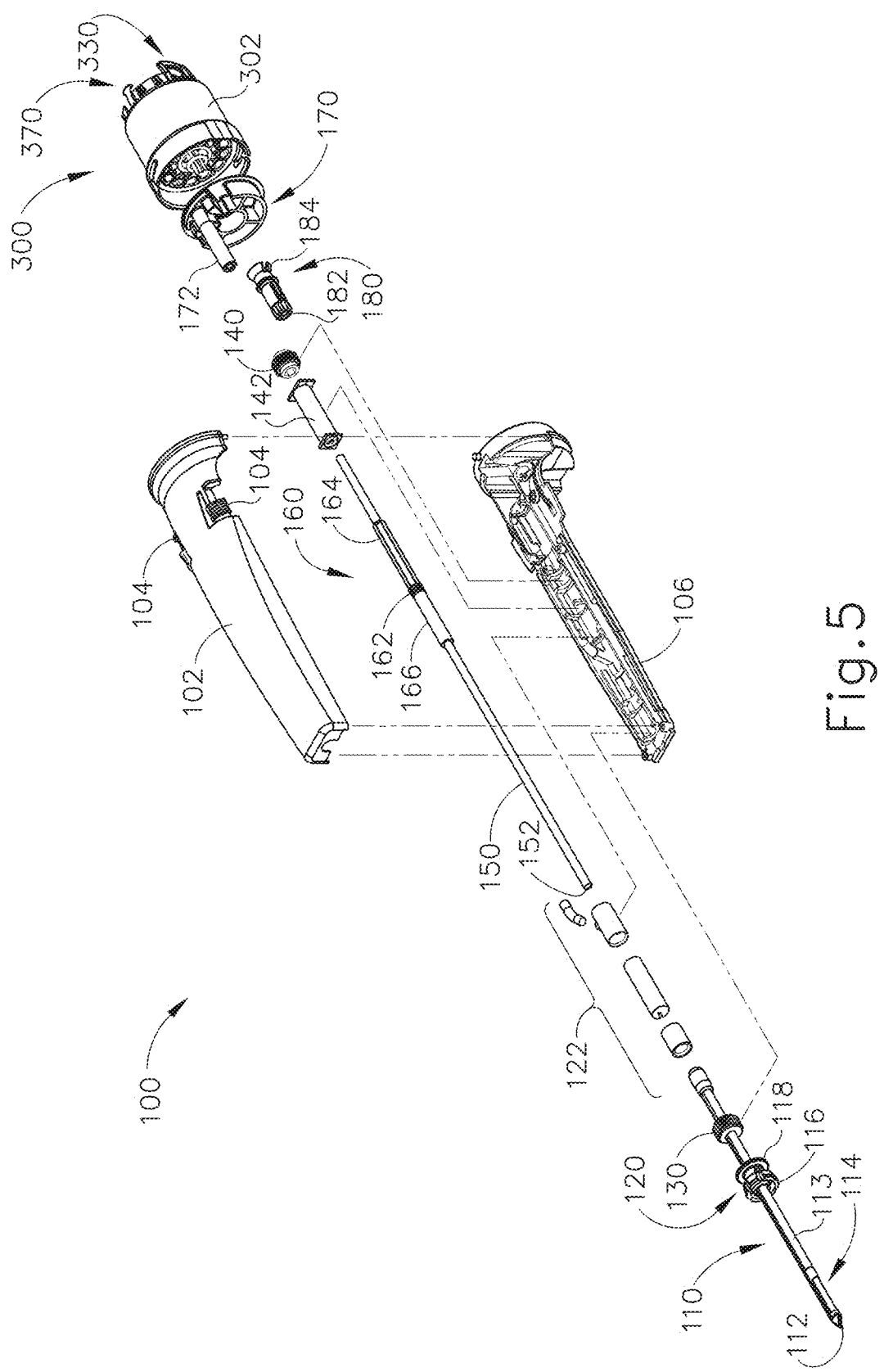
FIG. 5 depicts an exploded view of the probe of FIG. 4.
Figure 7:
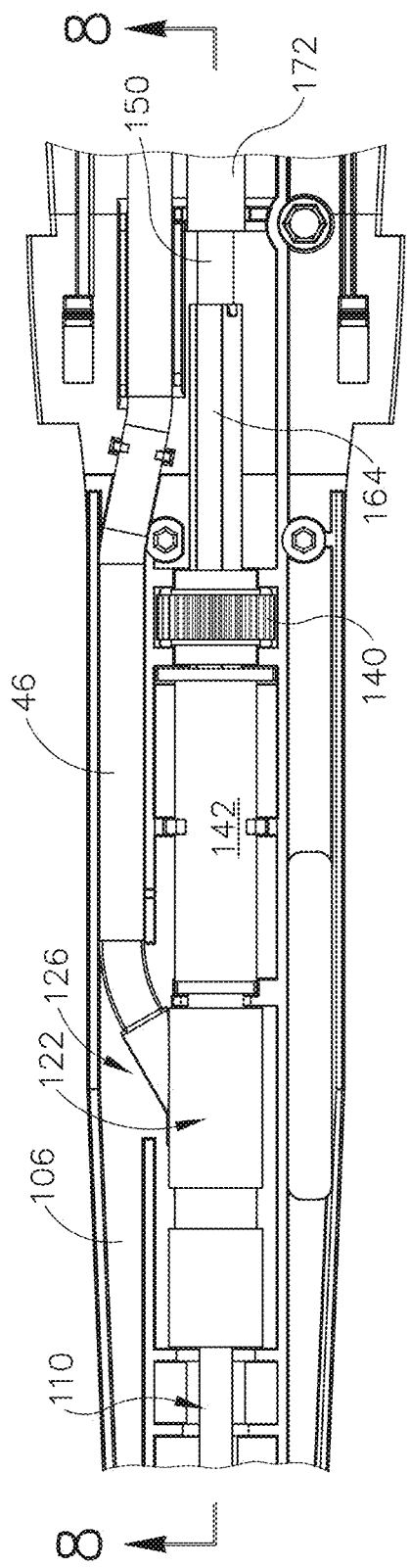
FIG. 7 depicts a partial top plan view of components of the probe of FIG. 4, with a top housing piece removed.

As noted above, cutter (150) is operable to simultaneously translate and rotate relative to needle (110) to sever a tissue sample from tissue protruding through lateral aperture (114). As best seen in FIGS. 5-7 cutter (150) includes an overmold (160) that is unitarily secured to cutter (150). Overmold (160) includes a generally smooth and cylindraceous distal portion (166), threading (162) in a mid-region of overmold (160), and a set of hexagonal flats (164) extending along a proximal portion of overmold (160). Distal portion (166) extends into manifold (122). Manifold (122) seals against distal portion (166) such that manifold (122) such that manifold (122) maintains the fluid tight coupling between second lumen (192) and tube (46) even when cutter (150) is translated and rotated relative to manifold (122).

Figure 8:
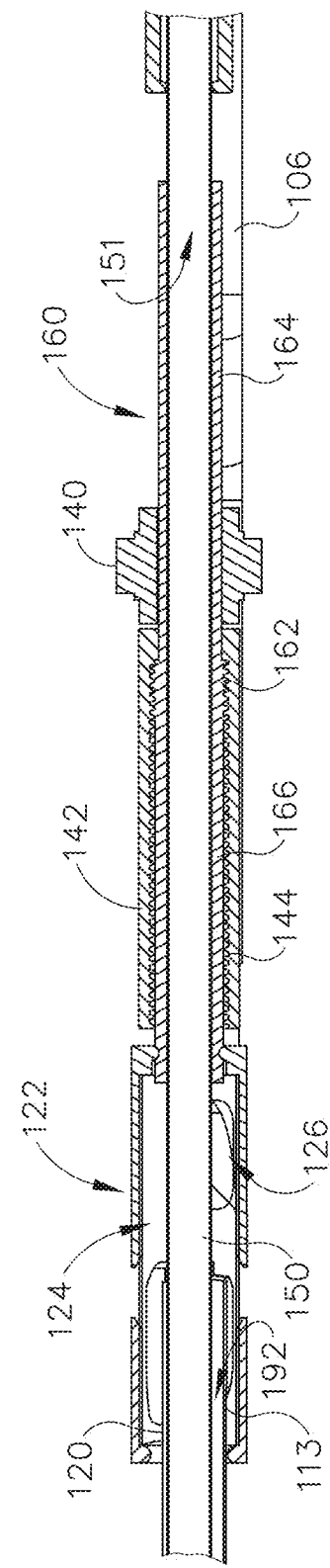
FIG. 8 depicts a side cross-sectional view of the components of FIG. 7, taken along line 8-8 of FIG. 7.

A gear (140) is positioned on flats (164) and includes a set of internal flats (not shown) that complement flats (164). Thus, gear (140) rotates overmold (160) and cutter (150) when gear (140) is rotated. However, overmold (160) is slidable relative to gear (140), such that cutter (150) may translate relative to chassis (160) despite gear (140) being longitudinally fixed relative to chassis (160). Gear (140) is rotated by gear (230). As best seen in FIGS. 7-8, a nut (142) is associated with threading (162) of overmold (160). In particular, nut (142) includes internal threading (144) that meshes with threading (162) of overmold (160). Nut (142) is fixedly secured relative to chassis (160). Thus, when gear (140) rotates cutter (150) and overmold (160), cutter (150) will simultaneously translate due to the meshing of threading (144, 162). In some versions, the foregoing cutter actuation components are further configured in accordance with at least some of the teachings of U.S. Pub. No. 2008/0214955, the disclosure of which is incorporated by reference herein. As yet another merely illustrative example, cutter (150) may be rotated and/or translated using pneumatic motors, etc. Still other suitable ways in which cutter (150) may be actuated will be apparent to those of ordinary skill in the art in view of the teachings herein.

C. Exemplary Tissue Sample Holder Assembly

Tissue sample holder (300) of the present example provides a plurality of discrete chambers that are configured to receive tissue samples that are severed by cutter (150) and communicated proximally through lumen (151) of cutter (150). In particular, and as will be described in greater detail below, tissue sample holder (300) includes tissue receiving trays (330) that are removably engaged with a rotatable member (310). Rotatable member (310) is removably engaged with a grasping feature (184) of a rotation member (180). Rotation member (180) is longitudinally fixed relative to chassis (106) yet is rotatable relative to chassis (106). Rotation member (180) includes an integral gear (182), which meshes with gear (240) of holster (200) when probe (100) and holster (200) are coupled together. Gears (182, 240) cooperate to rotate rotatable member (310) to index tissue chambers relative to lumen (151) of cutter (150) as will be described in greater detail below. A transparent cover (302) is positioned about rotatable member (310) and is removably secured to chassis (106). While bayonet features provide coupling between cover (302) and chassis (106), it should be understood that any suitable type of coupling may be used. Rotatable member (310) is freely rotatable within cover (302). However, rotatable member (310) is engaged with cover (302) such that rotatable member (310) will decouple relative to chassis (106) when cover (302) is removed from chassis (106). In other words, rotatable member (310) may be selectively coupled with and removed relative to chassis (106) by coupling and removing cover (302) from chassis (106).

Figure 11:
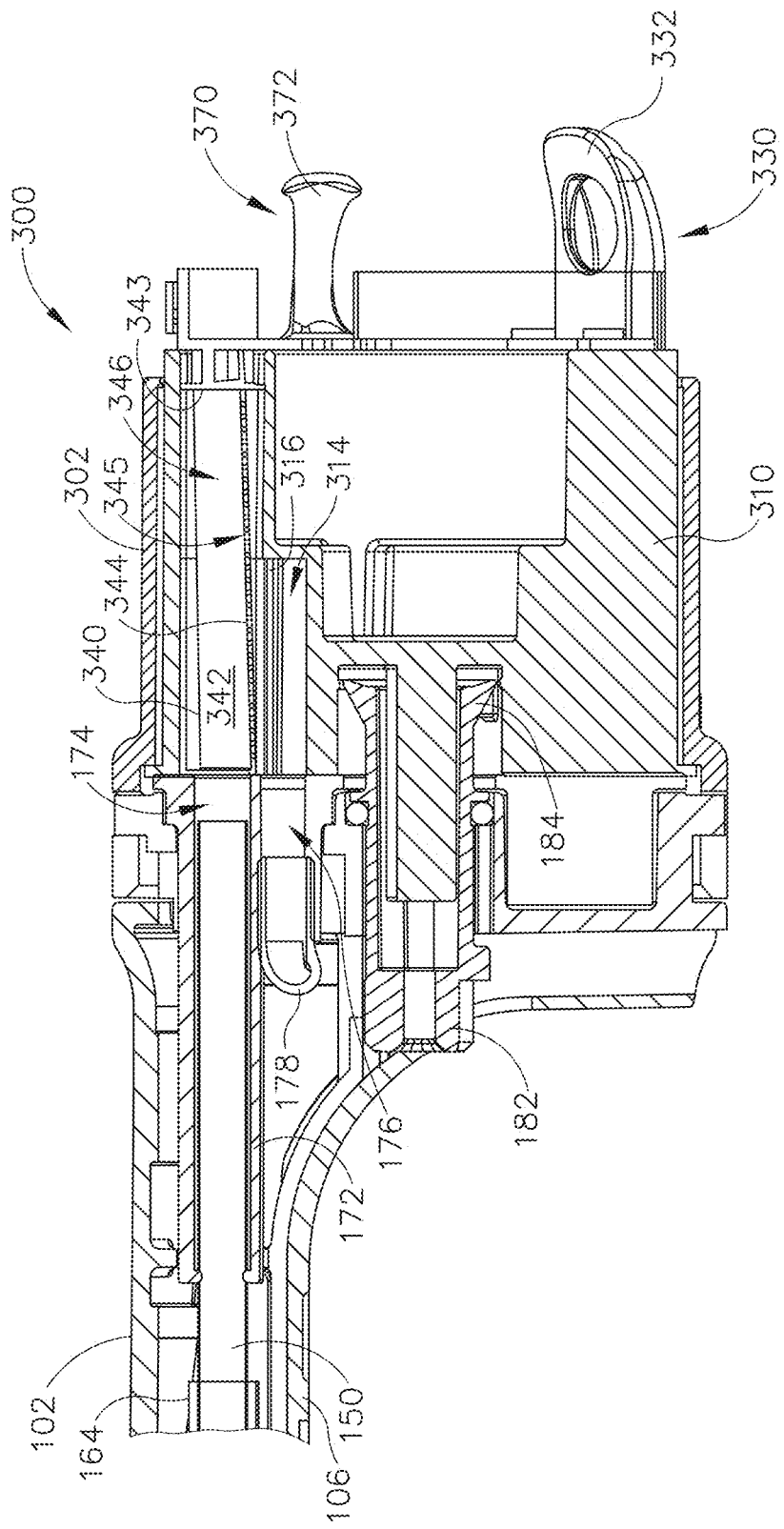
FIG. 11 depicts a side cross-sectional view of the tissue sample holder assembly of FIG. 9, with a tissue sample chamber aligned with the cutter.
Figure 12:
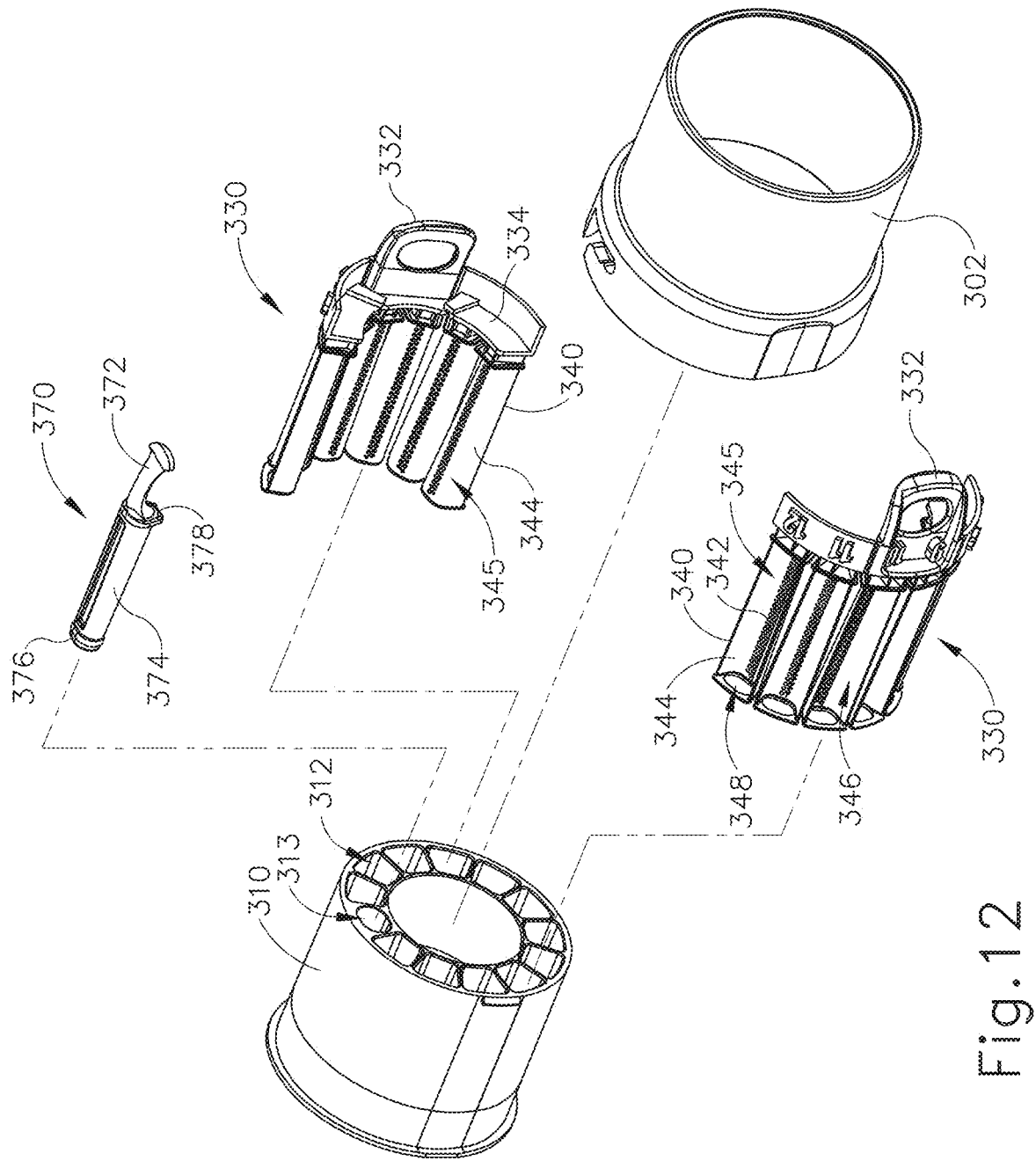
FIG. 12 depicts an exploded view of the tissue sample holder assembly of FIG. 9.

As best seen in FIG. 12, rotatable member (310) of the present example generally comprises a rotatable member and defines a plurality of chambers in the form of passages (312) that extend longitudinally through rotatable member (310) and that are angularly arrayed about the central axis of rotatable member (310). A lateral recess (314) (FIG. 11) is associated with a distal portion of each passage (312). Shelves (316) demarcate boundaries between each passage (312) and the associate lateral recess (314). As will be described in greater detail below, passages (312) receive trays (330) while recesses (314) provide pneumatic passages. An additional passage (313) and recess (315) are associated with a plug (360), as will also be described in greater detail below. Rotatable member (310) also includes a central shaft (320), which is configured to removably engage grasping feature (184). Central shaft (320) couples with grasping feature (184) upon coupling of outer cup (302) with chassis (106), as described above. Engagement between central shaft (320) and grasping feature (184) provides rotation of rotatable member (310) upon rotation of gear (182).

Figure 9:
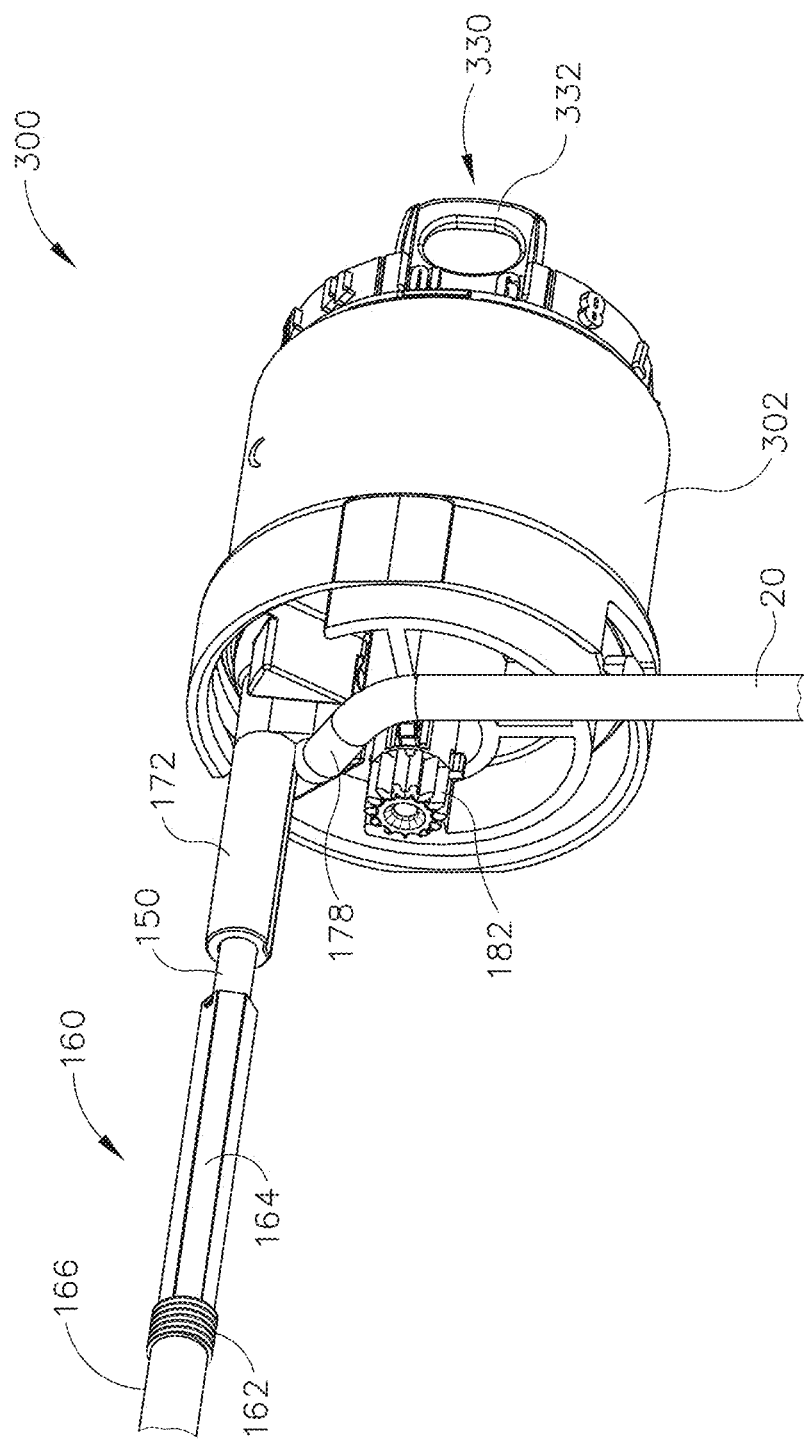
FIG. 9 depicts a perspective view of a tissue sample holder assembly of the probe of FIG. 4.
Figure 10:
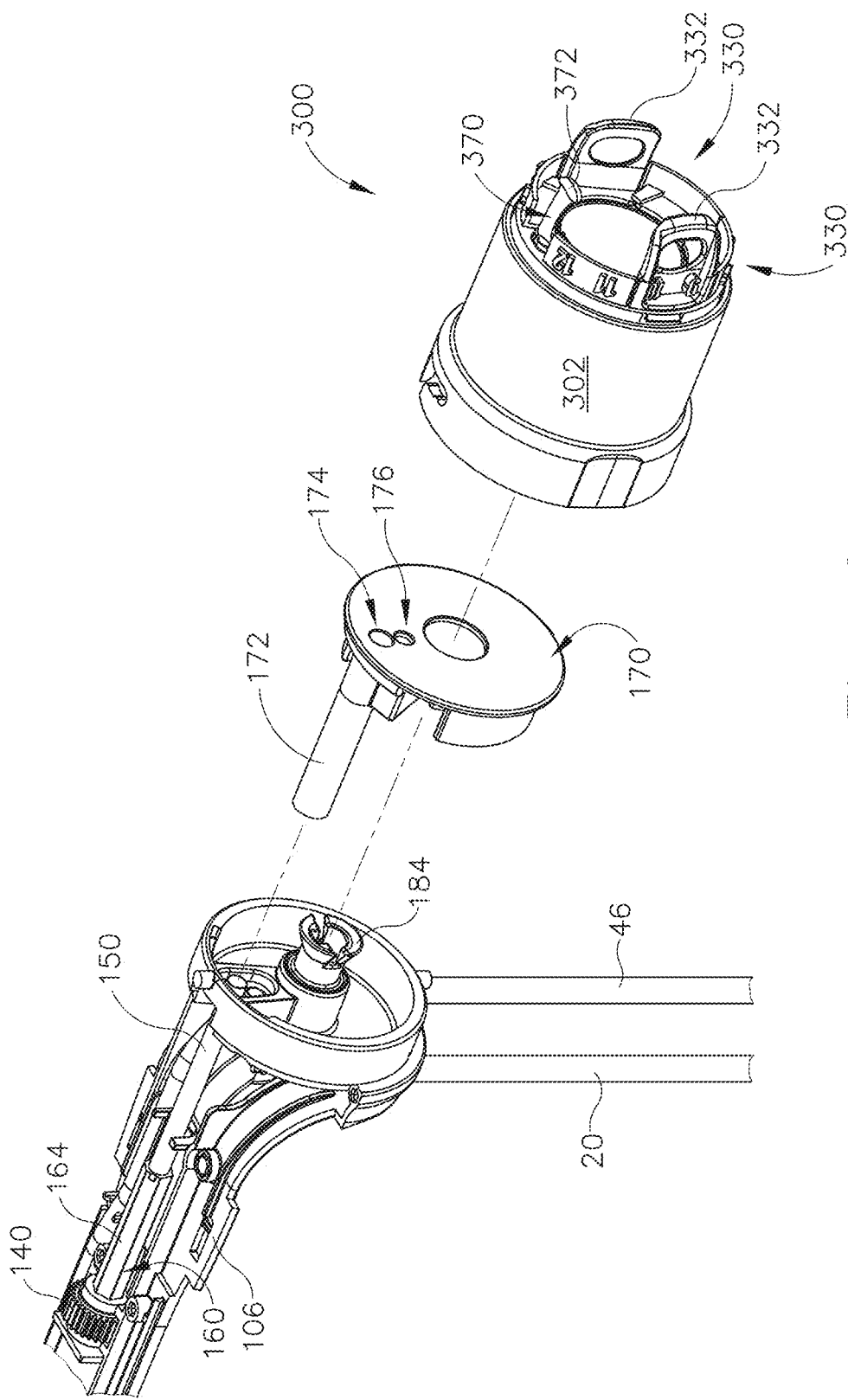
FIG. 10 depicts an exploded view of a proximal end of the probe of FIG. 4.

As best seen in FIGS. 10-11, a sealing member (170) is provided at the proximal end of chassis (106) and interfaces with the distal face of rotatable member (310). In the present example, sealing member (170) comprises rubber, though it should be understood that any other suitable material(s) may be used. Sealing member (170) includes a longitudinally extending cutter seal (172), which receives cutter (150) and seals against the exterior of cutter (150). The proximal end of cutter (150) remains within cutter seal (172) throughout the full range of travel of cutter (150). Cutter seal (172) maintains a fluid tight seal against cutter (150) during this full range of motion, including during rotation and translation of cutter (150). An opening (174) is positioned at the proximal end of cutter seal (170). This opening (174) is configured to align with whichever passage (312, 313) is at the 12 o'clock position. Another opening (176) is positioned below opening (174). Opening (176) is configured to align with whichever recess (314, 315) is at the 12 o'clock position. As best seen in FIGS. 9 and 11, opening (176) is in fluid communication with a port (178), which is coupled with tube (20). Thus, sealing member (170) provides fluid communication between tube (20) and whichever recess (314, 315) is at the 12 o'clock position. As will be described in greater detail below, rotatable member (310) further provides fluid communication between such recess (314, 315) and the associated passage (312, 313) at the 12 o'clock position; and thereby further to lumen (151) of cutter (150).

In other words, sealing member (170) and rotatable member (310) cooperate to provide fluid communication between tube (20) and lumen (151) of cutter (150) via whichever passage (312, 313) and recess (314, 315) are at the 12 o'clock position. It should be understood that sealing member (170) of the present example maintains a fluid tight seal against the distal face of rotatable member (310), even as rotatable member (310) is rotated relative to sealing member (170).

As noted above, tissue sample holder trays (330) are configured to removably engage rotatable member (310). Each tissue sample holder tray (330) of the present example includes a grip (332), a proximal wall (334), and a plurality of strips (340) extending distally from proximal wall (334). Strips (340) are sized and configured for insertion into associated passages (312) of rotatable member (310). Each strip (340) includes a pair of sidewalls (344) and a floor (342). Each pair of sidewalls (344) and floor (342) together define a corresponding tissue sample chamber (346). An opening (348) is provided at the distal end of each tissue sample chamber (346). Opening is sized and positioned to correspond with opening (174) of sealing member (170). Thus, the lumen (151) of cutter (150) is in fluid communication with the tissue sample chamber (346) of the strip (340) inserted in the passage (312) that is at the 12 o'clock position. As best seen in FIG. 11, strips (340) are configured such that the distal portion of each strip (340) receives support from a corresponding shelf (316) of rotatable member (310). Each floor (342) includes a plurality of openings (345) that provide fluid communication between tissue sample chamber (346) of strip (340) and lateral recess (314) of the passage (312) associated with strip (340). Thus, vacuum, atmospheric air, etc. that is communicated to opening (176) via tube (20) is further communicated to lumen (151) of cutter (150) via lateral recess (314), openings (345), and tissue sample chamber (346). During operation of biopsy device (10), tissue samples severed by distal edge (152) of cutter (150) are communicated proximally through the lumen (151) of cutter (150) and are then deposited into the tissue sample chamber (346) that is aligned with lumen (151) of cutter (150). Rotatable member (310) is rotated to successively align tissue sample chambers (346) with lumen (151) of cutter (150), enabling several tissue samples to be separately deposited in different tissue sample chambers (346) during operation of biopsy device (10). Bodily fluids and saline, etc. that are pulled through lumen (151) will pass through tissue sample holder (300) and tube (20) and are eventually deposited in vacuum canister (70).

Each strip (340) also includes a pair of wiper seals (343, 349) that seal against the interior of passage (312) when strip (340) is fully inserted into passage (312). Wiper seals (343, 349) provide a fluid tight seal for tissue sample chambers (346) and further provide frictional resistance to removal of strips (340) from rotatable member (310). Grips (332) are configured to facilitate removal of strips (340) from rotatable member (310), such as during or after a biopsy procedure to retrieve or otherwise directly observe tissue samples deposited in tissue sample chambers (346). Trays (330) also include numerical indicia (338) associated with each tissue sample chamber (346). In addition, trays (330) include pinched regions (336) that facilitate flattening of trays (330). In particular, pinched regions (336) provide sufficient flexibility to enable trays (330) to form an arcuate configuration for insertion into rotatable member (310); while also enabling trays (330) to form a generally flat configuration such as after trays (330) are removed from rotatable member (310) for inspection of tissue samples in trays (330).

It should be understood that rotatable member (310) and/or trays (330) may be configured in numerous other ways. By way of example only, rotatable member (310) and/or trays (330) may be configured in accordance with at least some of the teachings of U.S. Pat. Pub. No. 2008/0214955, the disclosure of which is incorporated by reference herein. As another merely illustrative example, rotatable member (310) and/or trays (330) may be configured in accordance with at least some of the teachings of U.S. Pat. No. 8,702,623, the disclosure of which is incorporated by reference herein. It should also be understood that tissue sample holder (300) need not necessarily position chambers (346) coaxially with lumen (151) of cutter (150). Tissue sample holder (300) may index chambers (346) relative to cutter (150) in any other suitable fashion. For instance, chambers (346) may extend along axes that are always offset from the axis of lumen (151), along axes that are oblique or perpendicular relative to the axis of lumen (151), or along other axes. Similarly, it should be understood that rotatable member (310) may rotate about an axis that is oblique or perpendicular relative to the axis of lumen (151). Still other suitable configurations will be apparent to those of ordinary skill in the art in view of the teachings herein.

As best seen in FIG. 12, and as noted above, tissue sample holder (300) of the present example includes a plug (360) that is received in a dedicated passage (313) of rotatable member (310). Plug (360) includes a grip (362) and a longitudinally extending body (364). Body (364) extends through part of the length of passage (313), distally terminating at the longitudinal position corresponding with the proximal end of recess (315). Plug (360) includes a pair of seals (366, 368) that seal against the interior of passage (313) when plug (360) is fully inserted in passage (313). Seals (366, 368) thus keep passage (313) fluid tight when plug (360) is inserted in passage (313). Passage (313) is configured to receive the shaft of a biopsy site marker applier. Passage (313) may also receive an instrument for delivering medicine, etc. to a biopsy site. By way of example only, passage (313) may receive an adapter configured to provide an interface between passage (313) and a conventional medicine deliver device. An example of such an adapter and other uses/configurations for a passage like passage (313) are described in U.S. Pat. No. 8,118,755, the disclosure of which is incorporated by reference herein. Plug (360) and/or passage (313) may also be configured and operable in accordance with at least some of the teachings of U.S. Pat. No. 8,938,285, the disclosure of which is incorporated by reference herein. Still other suitable configurations will be apparent to those of ordinary skill in the art in view of the teachings herein. In some other versions, plug (360) and/or passage (313) are simply omitted.

As described above, tissue sample holder (300) is generally configured to collect a plurality of tissue samples individually in discrete tissue sample trays (330). However, it should be understood that in some examples it may be desirable to collect a plurality of tissue samples is a single chamber. By way of example only, such a feature may be desirable where tissue samples are collected merely for removal of tissue from a patient, rather than for diagnostic purposes. Of course, in such circumstances, tissue samples collected in a single chamber may later be used for diagnostic purposes, even if the original intent was merely for tissue removal. In addition or in alternative, some operators may prefer collecting a plurality of tissue samples in a single chamber rather than individual chambers when collecting tissue samples for diagnostic purposes. In still further instances, an operator may desire to alternate between the modes described above to briefly analyze tissue sample quality using an individual tissue sample mode of collection and then proceed to a bulk tissue sample mode of collection for collection of tissue samples in the same general anatomical area. Thus, it should be understood that in some examples it may be desirable to include a means of bulk tissue collection in a tissue sample holder similar to tissue sample holder (300) described above.

IV. EXEMPLARY IMAGING SYSTEM

In some instances, it may be beneficial to immediately examine a recently biopsied tissue specimen through certain imaging modalities to thereby quickly analyze and assess the tissue properties. However, an operator may be limited in how quickly the tissue sample can be analyzed by an imaging device due to the time elapsed extracting the tissue sample from the biopsy device, positioning the tissue sample into an examination container, and subsequently inserting the examination container into an imaging system to produce images of the specimen for analysis. A biopsy device that is adapted to directly associate with an imaging system may be beneficial to reduce the amount of time and effort required to analyze a tissue sample during a biopsy procedure. Furthermore, being able to take an immediate image of a tissue specimen that was recently biopsied from a patient allows an operator to confirm whether the targeted tissue was successfully acquired at each instance of tissue extraction, thereby reducing the number of tissue samples extracted from the patient.

In biopsy devices such as device (10) described above, it may be beneficial to configure the components of the device, such as tissue sample holder (300), to cooperate with certain imaging modalities to thereby simplify the process for an operator to obtain and review graphical representations or other images of the biopsied tissue specimen. This practice may eliminate several intermediate steps required in generating images of a biopsied specimen and thus maximize the effectiveness of analyzing the characteristics of a tissue sample of a patient. It may be further desirable to integrate the imaging system with a biopsy device into a single assembly, while in other instances it may be desirable to adapt the biopsy device to function in association with a separate imaging modality.

The following description provides various examples of a biopsy device and corresponding imaging system that are cooperatively configured to produce images of a recently biopsied tissue sample prior to the removal of the specimen from the biopsy device. Ultimately, the association of the biopsy device with certain imaging modalities may be beneficial to ensure an operator is able to receive any pertinent data from the generated image in a timely manner. It should be understood that the imaging systems described below may be readily incorporated into any of the various biopsy devices (10) described above and utilized in any of the various surgical procedures described in the various references described herein. Other suitable ways in which the below-described biopsy devices and imaging systems may be used will be apparent to those of ordinary skill in the art in view of the teachings herein.

A. Biopsy Device with Sensor-Receiving Cavity

Figure 13:
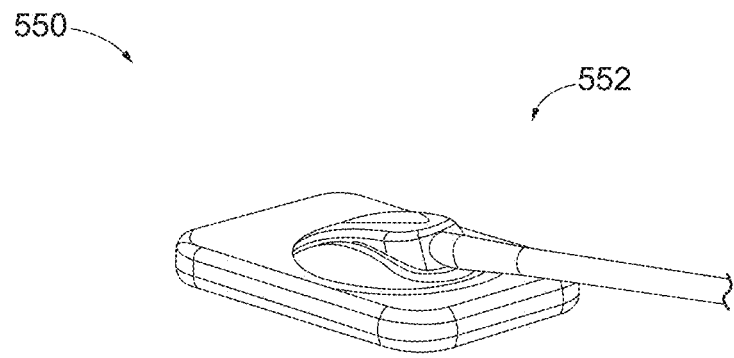
FIG. 13 depicts a perspective view of an exemplary digital sensor.
Figure 14:
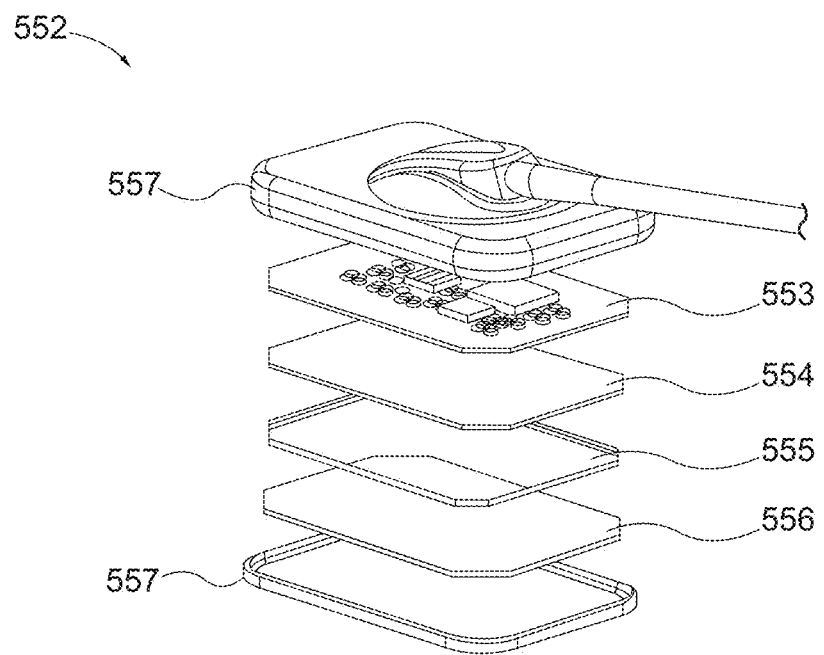
FIG. 14 depicts an exploded perspective view of the digital sensor of FIG. 13.
Figure 15:
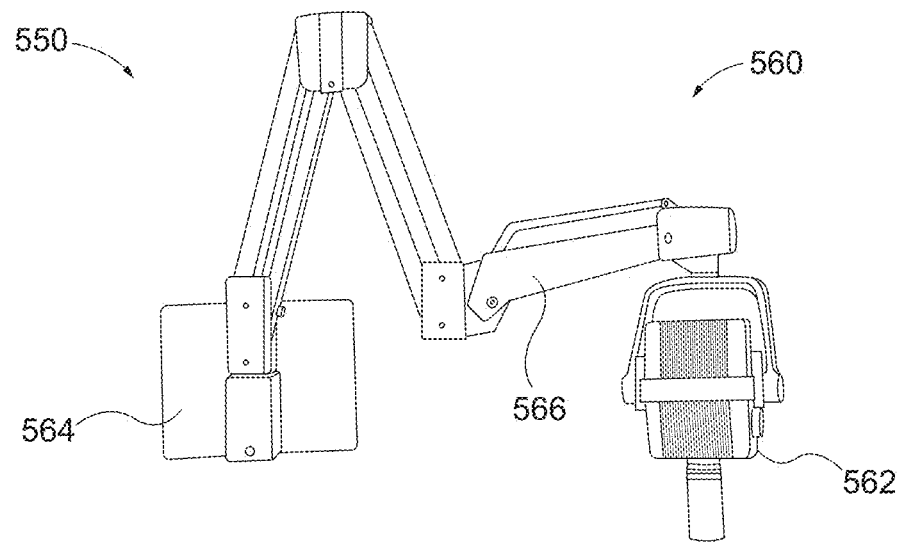
FIG. 15 depicts a perspective view of an exemplary imaging device.

As shown in FIGS. 13-15, an exemplary imaging system (550) comprises a sensor (552) and an imaging device (560). In the present example, sensor (552) is generally configured as a digital sensor, but in other examples sensor (552) can include any other suitable sensor. For instance, in some examples sensor (552) comprises a charge-coupled device (CCD) sensor, a complementary metal-oxide semiconductor (CMOS) sensor, indium gallium arsenide sensors, conventional film, and/or any other sensor as will be apparent to those of ordinary skill in the art. Particularly, as shown in FIGS. 13-14, sensor (552) includes an electronic circuit (553), an imager (554), a fiber optic plate (555) and a scintillator (556) encapsulated within an outer casing (557). Sensor (552) is a diagnostic imaging sensor that is operable to convert and transmit data digitally.

Although not shown, it should be understood that sensor (552) may include additional or alternative internal components than those depicted. For example, sensor (552) may include components corresponding to those included in an interline transfer CCD sensor, frame transfer CCD sensor, on-chip A/D conversion CMOS sensor, off-chip A/D conversion CMOS sensor, those used in short-wave infrared (SWIR) imaging, or thermal imaging. Such internal components of sensor (552) may include various transistors, pixels (photodiodes or photocapacitors), and/or other components as will be apparent to those of ordinary skill in the art. The size and shape of the pixels in sensor (552) may vary to optimize, among other things, the imaging optics, saturation capacities, and signal-to-noise ratios, resolution, spatial frequencies and contrast. The overall size of sensor (552) may also vary to optimize the system's field of view. By way of example only, sensor (552) may be sized as ½", ⅓", ½", 1/1.8", ⅔", 1", 1.2" or any other size as will be apparent to those of ordinary skill in the art.

As seen in FIG. 15, imaging device (560) includes a head (562), a base (564) and an extension arm (566) extending therebetween. Extension arm (566) is configured to extend and pivot about base (564) to thereby allow for the selective positioning of head (562). Imaging device (560) is operable to communicate with sensor (552) by transmitting a high-energy beam (e.g., x-ray, etc.) through air until encountering sensor (552) (see FIG. 18). In particular, head (562) is configured to transmit high-energy beams outwardly upon actuation of imaging device (560). As will be described in greater detail below, any intermediate objects positioned between head (562) and sensor (552), i.e. a biopsied tissue sample, will interact with the high-energy rays transmitted by imaging device (560) and be identified and depicted in a corresponding image generated by imaging system (550). By way of example only, imaging system (550) may be operable to generate x-ray images (e.g., radiography images), optical coherence tomography images, multipicture or videos, high definition ultrasound images, or other images as will be apparent to those of ordinary skill in the art in view of the teachings herein.

Figure 16A:
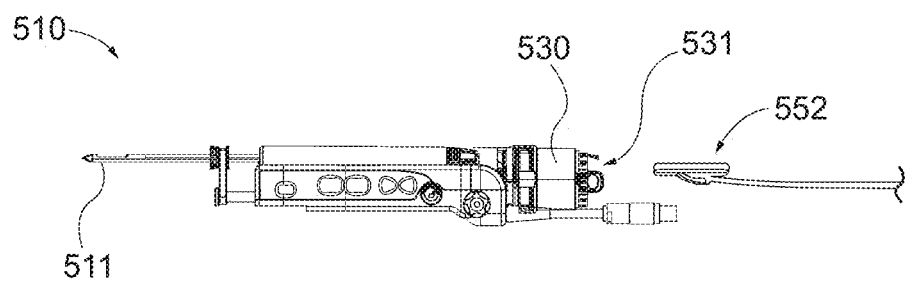
FIG. 16A depicts a side elevational view of the biopsy device of FIG. 2, with the digital sensor of FIG. 13 being advanced towards the tissue sample holder assembly of FIG. 9.
Figure 17A:
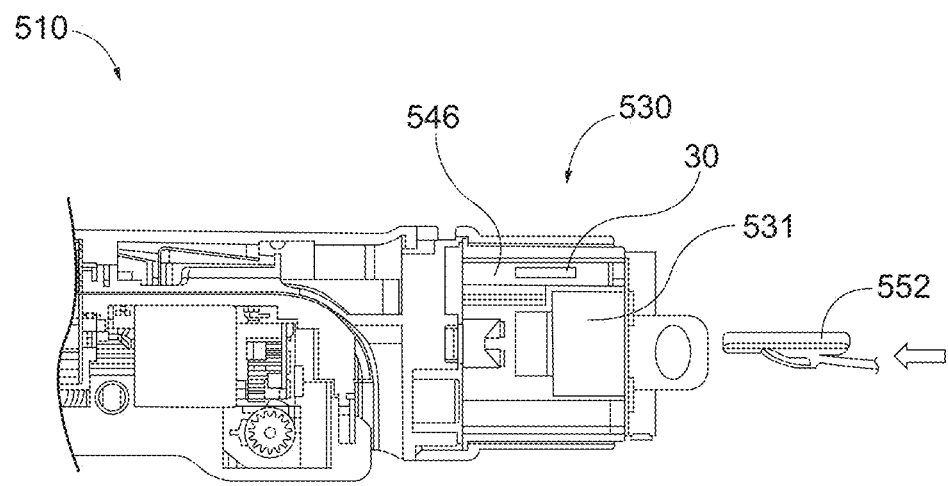
FIG. 17A depicts a side cross-sectional view of the biopsy device of FIG. 16A.

FIG. 16A shows a biopsy device (510) including a needle (511) attached on a distal end and a tissue sample holder (530) attached on a proximal end, respectively. It should be understood that biopsy device (510), needle (511), and tissue sample holder (530) of this example may be configured and operable just like biopsy device (10), needle (110), and tissue sample holder (300), respectively, described above, except for the differences explicitly noted herein. As best seen in FIG. 17A, tissue sample holder (530) includes an internal cavity (531) centrally positioned about multiple tissue sample chambers (546). Internal cavity (301) is sized and shaped to receive sensor (552) therein.

Figure 16B:
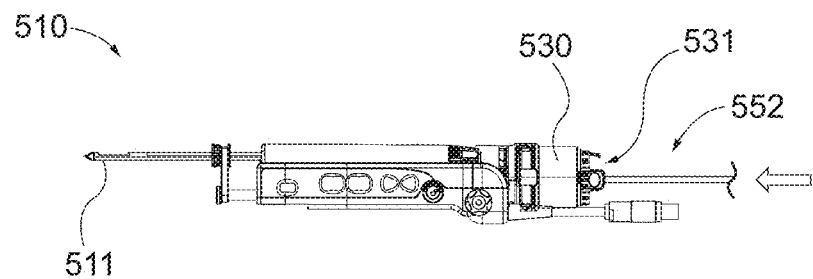
FIG. 16B depicts the side elevational view of the biopsy device similar to FIG. 16A, but with the digital sensor positioned within the tissue sample holder assembly.
Figure 17B:
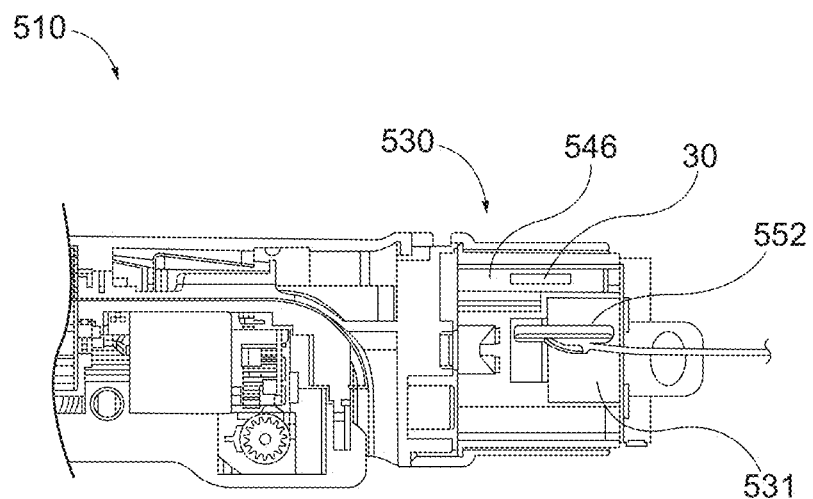
FIG. 17B depicts a side cross-sectional view of the biopsy device of FIG. 16B.

In the present example, an operator grasps biopsy device (510), inserts needle (511) into a patient's breast, and collects one or a plurality of tissue samples (30) from the patient. Such tissue samples (30) may be pneumatically deposited in tissue sample holder (530). Rather than an operator detaching tissue sample holder (530) from biopsy device (510) to thereby retrieve tissue samples (30) for analysis, sensor (552) is slidably advanced towards a distal end of biopsy device (510), as seen in FIG. 16A. In particular, FIG. 16B shows sensor (552) aligned with tissue sample holder (530) such that sensor (552) is received by biopsy device (510) within tissue sample holder (530). As best seen in FIG. 17A, sensor (552) is slidably received within internal cavity (531) of tissue sample holder (530) such that sensor (552) is aligned with and facing one or more tissue sample chambers (546). In the present example, sensor (552) is facing upwardly from within internal cavity (531) towards one or more tissue sample chambers (546) that are directly above sensor (552), as seen in FIG. 17B. In this alignment, sensor (552) is ideally positioned to image the tissue sample (30) that is deposited within the tissue sample chamber (546) that is in fluid communication with needle (511).

Although sensor (552) in the present example is sized to extend adjacently to one or more tissue sample chambers (546), it should be understood that sensor (552) may be sized and shaped to extend adjacent to more or fewer tissue sample chambers (546). For instance, sensor (552) may be sized and shaped such that a single tissue sample (30) deposited within an individual tissue sample chamber (546) is capable of being imaged at a time. Alternatively, sensor (552) may have a greater size and shape such that multiple tissue samples (30) contained in multiple tissue sample chambers (546), respectively, may be imaged simultaneously.

Figure 17C:
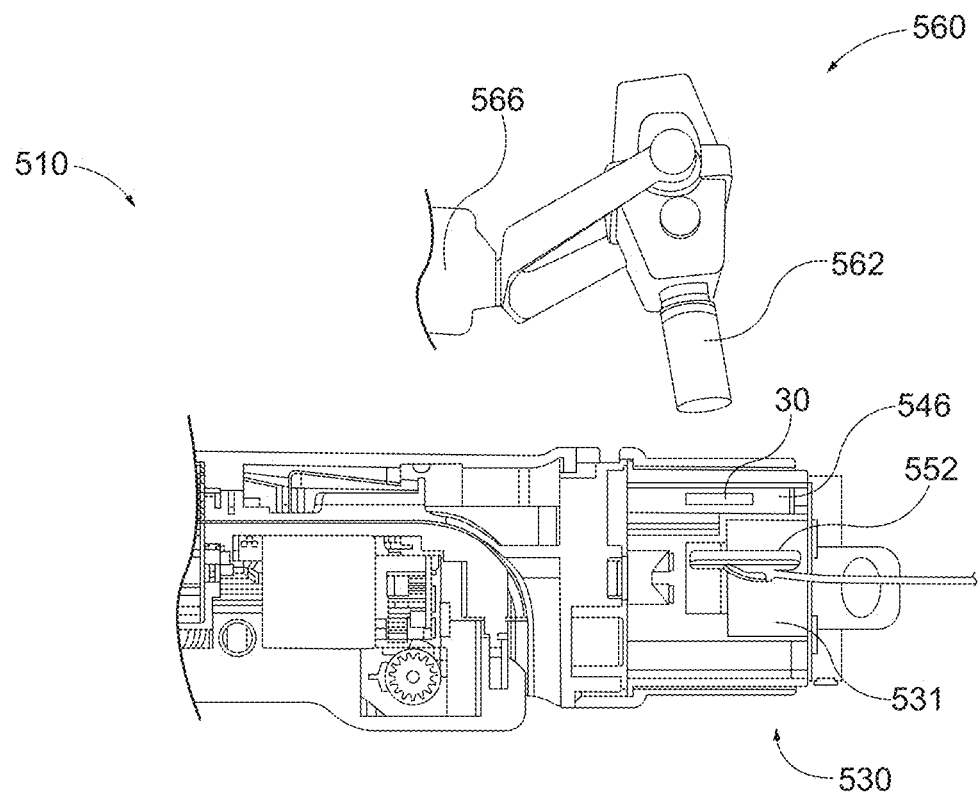
FIG. 17C depicts a side cross-sectional view of the biopsy device similar to FIG. 17B, but with the imaging device of FIG. 15 positioned adjacent to the tissue sample holder assembly.
Figure 18:
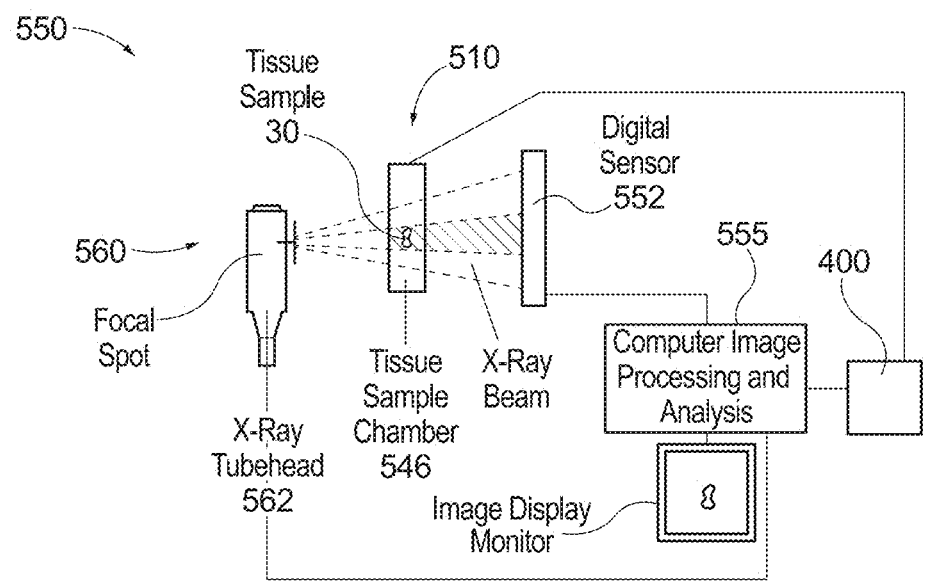
FIG. 18 depicts a schematic diagram of the imaging device of FIG. 15 transmitting a beam towards the digital sensor of FIG. 13, with the digital sensor outputting a processed image of the contents contained in the tissue sample holder assembly.

With sensor (552) inserted within internal cavity (531) of tissue sample holder (530), an operator selectively positions imaging device (560) directly above tissue sample holder (530) such that tissue sample chamber (546), containing tissue sample (30), is positioned between sensor (552) and head (562), as seen in FIG. 17C. In this instance, an operator activates imaging system (550) to transmit x-ray radiation from imaging device (560) towards tissue sample (30) until encountering sensor (552), as seen in FIG. 18. Tissue sample (30) absorbs some of the energy or radiation transmitted by head (562), and a corresponding image is generated by imaging system (550) processing x-rays received by sensor (552). In the present example, imaging system (550) is operable to transmit x-ray radiation from head (562) to sensor (552) thereby generate x-ray images. Although not shown, it should be understood that imaging system (550) may be operable to generate other images, including but not limited to, optical coherence tomography images, multipicture or videos, high definition ultrasound images, or other images as will be apparent to those of ordinary skill in the art in view of the teachings herein.

As a result, an image of tissue sample (30) is immediately generated by imaging system (550) for the benefit of an operator's timely review and assessment. In the present example, an operator is not required to initially disassemble tissue sample holder (530) from biopsy device (510), to subsequently remove tissue sample (30) from tissue sample chamber (546) for subsequent placement into an examination container (not shown) before being able to generate an image of sample (30). An operator rotates tissue sample holder (530) relative to the body of biopsy device (510) such that tissue sample chambers (546) are repositioned. In this instance, a different tissue sample chamber (546) is positioned directly above sensor (552) such that the tissue sample (30) located within this tissue sample chamber (546) is now positioned between head (562) and sensor (552) for examination. An operator may continue to rotate tissue sample holder (530) while maintaining sensor (552) at a fixed orientation, facing upwardly, to effectively image multiple tissue samples (30) that are deposited into separate tissue sample chambers (546) of tissue sample holder (530). Alternatively, the orientation of tissue sample holder (530) may remain stationary as an operator rotates sensor (552) within internal cavity (531). In this instance, although not shown, imaging device (560) is similarly realigned to relative to tissue sample holder (530) to thereby direct head (562) towards the front face of sensor (552).

In some examples, imaging device (560) can be integrated into a patient support system or other systems associated with biopsy device (510) to promote multiple uses of imaging device (560). For instance, in some examples biopsy device (510) is used in connection with a stereotactic imaging system such as the MAMMOTEST stereotactic biopsy table manufactured by Devicor Medical Products, Inc. of Cincinnati, OH. In such systems, an x-ray source similar to imaging device (560) is mounted on a swivel arm to orient the x-ray source relative to patient. Where such a stereotactic imaging system is used, the x-ray source can be configured in lieu of imaging device (560). In such examples, modifications may be made to the stereotactic imaging system to provide enhanced flexibility for movement of the x-ray source relative to biopsy device (510).

As shown in FIG. 18, imaging system (550) can be in communication with control module (400) to promote coordination between biopsy device (510) and imaging system (550). For instance, in some examples imaging system (550) includes a computer (555) configured for image processing and control of imaging device (560). In this configuration, computer (555) generally controls the acquisition and processing of x-ray images. Computer (555) can be further in communication with control module (400) to send and receive signals to/from control module (400). In one exemplary use, this communication between control module (400) and computer (555) can be used to automate the imaging process. For instance, in some uses, control module (400) can be configured to provide an indication to computer (555) when a biopsy sample has been collected. In response to this communication, computer (555) can then begin an imaging process automatically to acquire an image of the collected tissue sample. Thus, the communication between computer (555) and control module (400) can be configured to provide automated imaging in real time.

B. Biopsy Device with an Integral Digital Sensor

Figure 19:
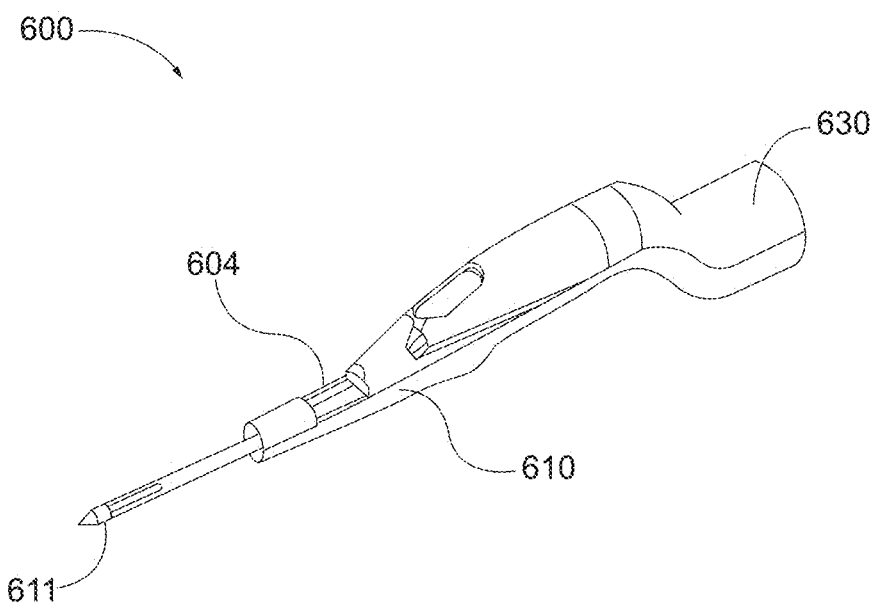
FIG. 19 depicts a perspective view of an exemplary alternative biopsy device, including a distal tissue sample viewing window.

FIG. 19 shows an exemplary alternative biopsy device (600) comprising a probe (610), a holster (620) and a tissue sample holder (630). Except as otherwise described below, biopsy device (600) and tissue sample holder (630) may be configured and operable just like biopsy device (10) and tissue sample holder (300), respectively, described above. Biopsy device (600) further comprises a tissue sample window (604) disposed proximally of the distal end of probe (610). Exemplary biopsy devices including tissue sample windows may be construed in accordance with the teachings of U.S. App. No. 62/505,571, entitled "Biopsy Device with Sterile Sleeve," filed on May 17, 2017, the disclosure of which is incorporated by reference herein.

In some examples, tissue sample window (604) exposes a gate assembly (not shown), such that the gate assembly is visible to an operator though probe (610). The gate assembly is generally configured to selectively arrest movement of the severed tissue sample (30) within the fluid conduit between the cutter and the tissue sample holder (630). The gate assembly enables the operator to temporarily cease progression of tissue sample (30) for visual inspection though tissue sample window (604) of probe (610). At least a portion of the gate assembly is coupled to cutter to communicate rotational and translational motion of gate assembly to cutter. Thus, it should be understood that rotation and translation of cutter drive member (not shown) results in corresponding rotation and translation of cutter via the coupling between at least a portion of the gate portion and at least a portion of the gate assembly. In some examples, the gate assembly may be constructed in accordance with the teachings of U.S. App. No. 62/429,379, entitled "Apparatus to Allow Biopsy Sample Visualization During Tissue Removal," filed on Dec. 2, 2016, the disclosure of which is incorporated by reference herein.

Figure 20:
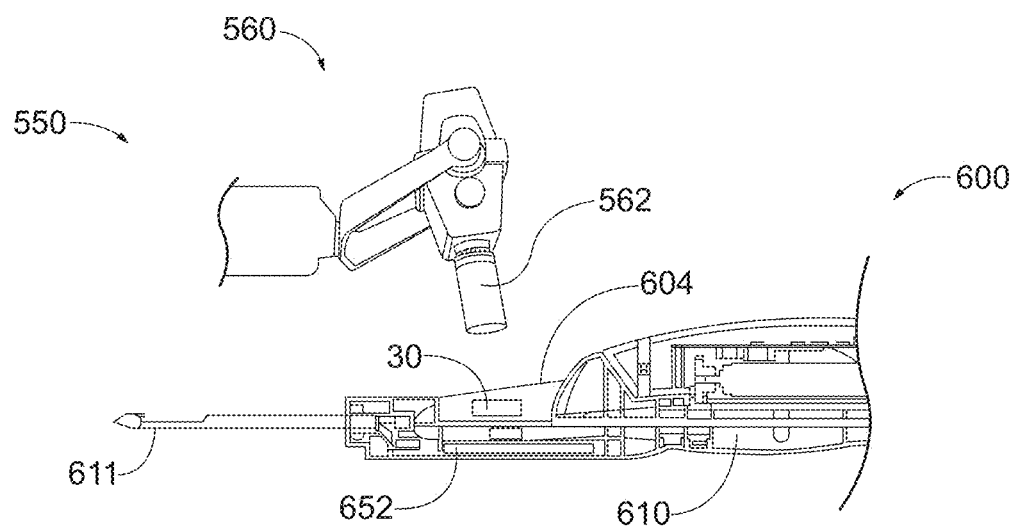
FIG. 20 depicts a side cross-sectional view of the biopsy device of FIG. 19, with the imaging device of FIG. 15 selectively positioned adjacent to the distal tissue sample viewing window.

As best seen in FIG. 20, biopsy device (600) includes a sensor (652) proximate to a distal end of probe (610). Sensor (652) is positioned below tissue sample window (604). It should be understood that sensor (652) of this example may be configured and operable just like sensor (552) described above, except for the differences explicitly noted herein. Sensor (652) has a longitudinal length substantially equal to, or greater than, the length of tissue sample window (604) such that any tissue sample (30) contained within tissue sample window (604) will not exceed beyond the dimensions of sensor (652) to thereby ensure a complete image of tissue sample (30) is attainable. Sensor (652) is a diagnostic imaging sensor that is operable to convert and transmit data digitally. Sensor (652) is a reusable sensor such that sensor (652) is operable to be inserted within probe (610) prior to a medical procedure and subsequently removed from biopsy device (600) after the procedure.

In the present example, after needle (611) is inserted into a patient's breast to collect tissue sample (30), tissue sample (30) is directed to tissue sample window (604) prior to being deposited into tissue sample holder (630). In this instance, as seen in FIG. 20, an operator selectively positions imaging device (560) directly above tissue sample window (604), containing tissue sample (30), such that tissue sample (30) is positioned between sensor (652) and head (562). In this instance, an operator activates imaging system (550) to transmit x-ray radiation from imaging device (560) towards tissue sample (30) until encountering sensor (652), resulting in the production of an image of tissue sample (30). As a result, an operator is able to analyze the tissue characteristics of sample (30) without needing to collect sample (30) within tissue sample holder (630) before removing tissue sample (30) for subsequent placement into an examination container (not shown) for imaging by imaging system (550). Once an image of tissue sample (30) has been generated from imaging system (550), an operator actuates the gate assembly (not shown) of biopsy device (600) to thereby transfer tissue sample (30) out of tissue sample window (604) and into tissue sample holder (630). In this instance, an operator may continue to actuate the cutter of needle (611) within a patient to thereby extract a second tissue sample (30) into tissue sample window (604) for examination.

Figure 21:
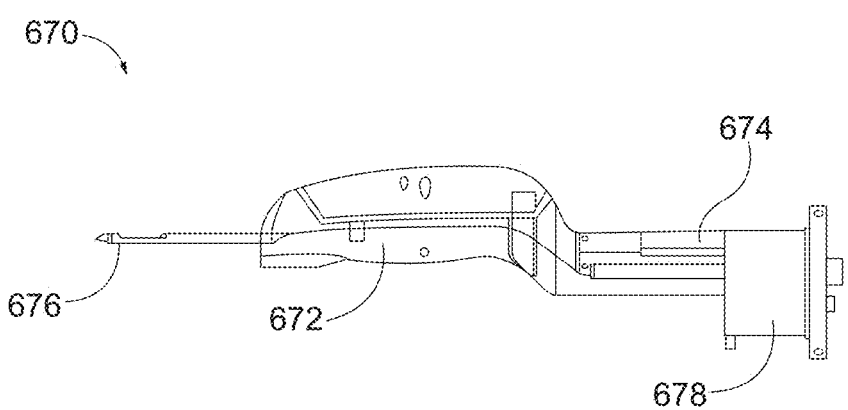
FIG. 21 depicts a side elevational view of another exemplary alternative biopsy device, including a proximal tissue sample viewing window.

In some instances, it may be desirable for the tissue sample window to be positioned distally adjacent to the tissue sample holder and proximally relative to the needle, such that the recently biopsied tissue sample (30) may be inspected by an operator at the proximal end of the biopsy device, which is closer to the operator. In this instance, the proximal positioning of the tissue sample window may provide an operator with an improved perspective of the tissue sample (30) deposited therein due to the closer proximity of the tissue sample window and the operator. As shown in FIG. 21, a biopsy device (670) includes a tissue sample window (674) positioned adjacently relative to a proximal end of device (670) such that tissue sample window (674) still receives tissue sample (30) from a needle (676) prior to being deposited in a tissue sample holder (678). In some examples, tissue sample window (674) may be associated with a gate assembly (not shown) incorporated into a portion of probe (610). The gate assembly is generally configured to selectively arrest movement of the severed tissue sample (30) within the fluid conduit between the cutter and tissue sample holder (678). The gate assembly enables the operator to temporarily cease progression of tissue samples (30) for visual inspection though tissue sample window (674). In some examples, the gate assembly may be constructed in accordance with the teachings of U.S. App. No. 62/429,379, entitled "Apparatus to Allow Biopsy Sample Visualization During Tissue Removal," filed on Dec. 2, 2016, the disclosure of which is incorporated by reference herein. Alternatively, biopsy device (670) may simply lack a gate assembly, such that severed tissue samples (30) are permitted to travel freely to tissue sample holder (678).

Figure 22:
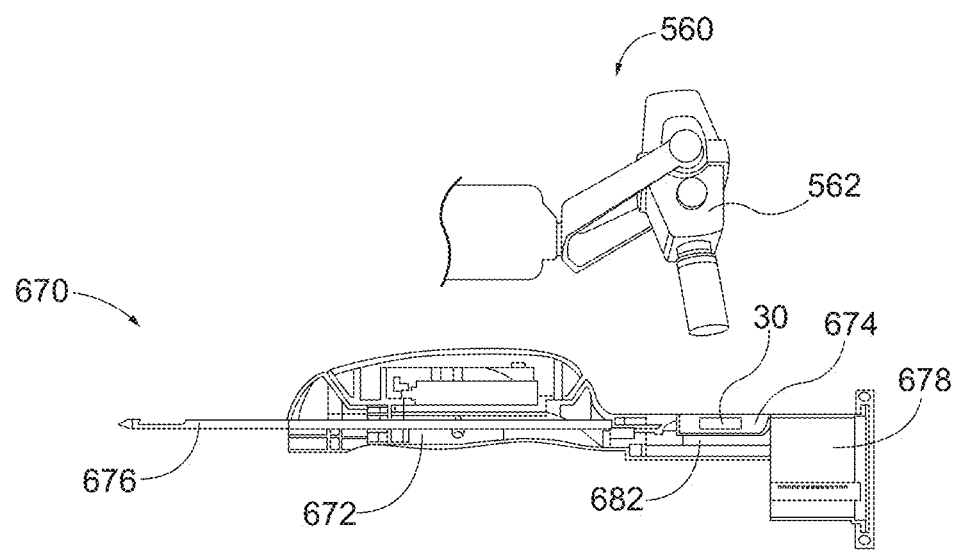
FIG. 22 depicts a side cross-sectional view of the biopsy device of FIG. 21, with the imaging device of FIG. 15 selectively positioned adjacent to the proximal tissue sample viewing window.

As best seen in FIG. 22, a sensor (682) is adjacent to a proximal end of a probe (672). As similarly shown in FIG. 20, sensor (682) is positioned below tissue sample window (674) and has a longitudinal length substantially equal to, or greater than, the length of tissue sample window (674). As such, any tissue sample (30) contained within tissue sample window (674) will not extend beyond the dimensions of sensor (682) to thereby ensure a complete image of tissue sample (30) is generated during each instance. In the present example, after needle (676) is inserted into a patient's breast to collect tissue sample (30), tissue sample (30) is directed to tissue sample window (674) prior to being deposited into tissue sample holder (678). In this instance, an operator selectively positions imaging device (560) directly above tissue sample window (674), containing tissue sample (30), such that tissue sample (30) is positioned between sensor (682) and head (562). With the proximal positioning of tissue sample window (674) relative to biopsy device (670), an operator is able to easily position imaging device (550) adjacent to tissue sample (30) as tissue sample window (674) is generally closer to an operator than tissue sample window (604) of biopsy device (600).

Once imaging device (560) is positioned as desired, an operator activates imaging system (550) to transmit x-ray radiation from imaging device (560) towards tissue sample (30) until encountering sensor (682), resulting in the production of an image of tissue sample (30). As a result, an operator is able to analyze the tissue characteristics of sample (30) without needing to collect sample (30) within tissue sample holder (678) before removing tissue sample (30) for subsequent placement into an examination container (not shown) for imaging by imaging system (550). Once an image of tissue sample (30) has been generated from imaging system (550), an operator actuates the gate assembly (not shown) of biopsy device (670) to thereby transfer tissue sample (30) out of tissue sample window (674) and into tissue sample holder (678). In this instance, an operator may continue to actuate the cutter of needle (676) within a patient to thereby extract a second tissue sample (30) from a patient and into tissue sample window (674) for examination.

C. Tissue Sample Holder with an Integral Digital Sensor

Figure 23:
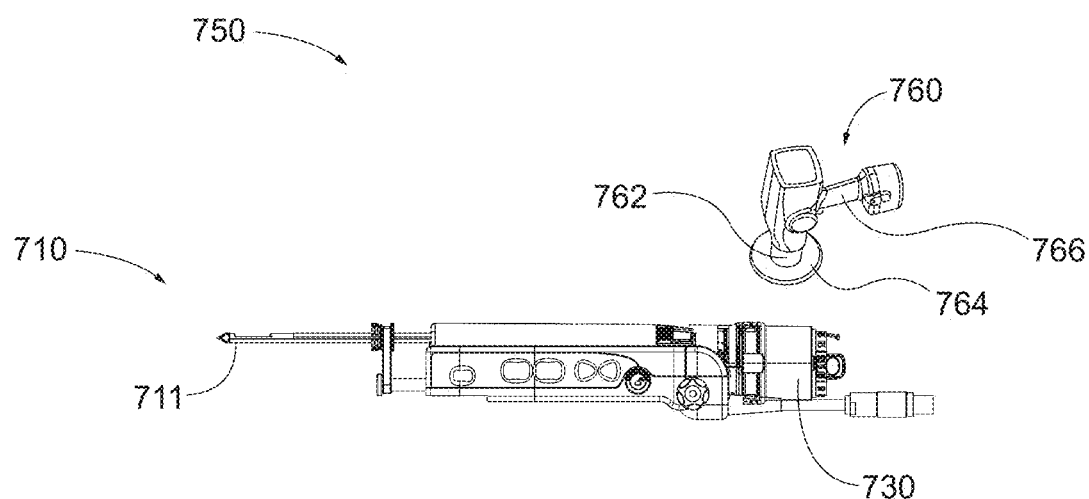
FIG. 23 depicts a side elevational view of the biopsy device of FIG. 2, with an exemplary alternative imaging device selectively positioned adjacent to the tissue sample holder assembly.

FIG. 23 shows an exemplary biopsy device (710) and an exemplary imaging system (750). Biopsy device (710) includes a needle (711) attached on a distal end and a tissue sample holder (730) attached on a proximal end, respectively. It should be understood that biopsy device (710), needle (711), and tissue sample holder (730) of this example may be configured and operable just like biopsy device (10), needle (110), and tissue sample holder (300), respectively, described above, except for the differences explicitly noted herein. Imaging system (750) includes an imaging device (760) and a sensor (752). It should be understood that imaging system (750), imaging device (760), and sensor (752) of this example may be configured and operable just like imaging system (550), imaging device (560), and sensor (552) described above, except for the differences explicitly noted herein. Imaging device (760) is a handheld device that includes a head (762), an external backscatter shield (764), a handgrip (766) and an actuation feature (768). Imaging device (760) is operable to communicate with sensor (752) by transmitting x-ray energy or radiation through air until encountering sensor (752). Head (762) is configured to transmit energy beams outwardly upon actuation of imaging device (760) via actuation feature (768). External backscatter shield (764) is positioned proximate to, and substantially around, head (762) such that head (762) is separated from a remaining portion of imaging device (760) by external backscatter shield (764). External backscatter shield (764) is operable to protect an operator from radiation exposure transmitted by head (762) when imaging device (760) is actuated.

Figure 24:
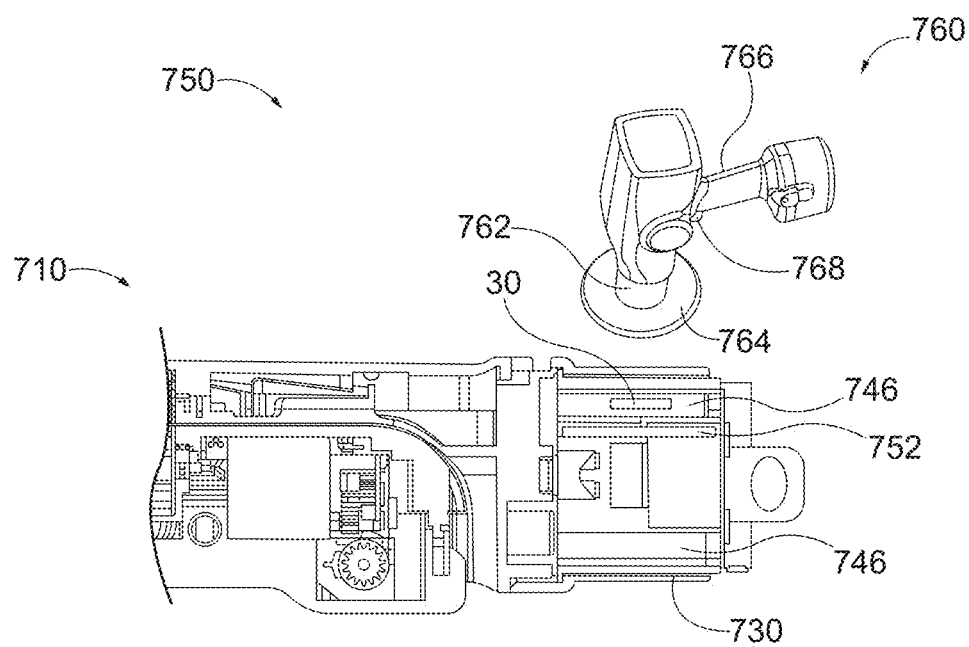
FIG. 24 depicts a side cross-sectional view of the biopsy device of FIG. 23, the biopsy device including an exemplary digital sensor positioned within the tissue sample holder assembly.

As best seen in FIG. 24, tissue sample holder (730) includes multiple tissue sample chambers (746) and a single sensor (752) positioned therein. In particular, sensor (752) is positioned immediately below the tissue sample chamber (746) that is positioned at the top of tissue sample holder (730). Sensor (752) is fixedly secured within tissue sample holder (730) such that sensor (752) maintains the relative position within tissue sample holder (730) as tissue sample chambers (746) are rotated within tissue sample holder (730). In this instance, sensor is aligned with and facing one or more tissue samples chambers (746) that are directly above and facing the front face of sensor (752). In this alignment, sensor (752) is ideally positioned to image the tissue sample (30) that is deposited within the tissue sample chamber (746) that is in fluid communication with needle (711). Although sensor (752) in the present example is sized to extend adjacently to one or more tissue sample chambers (746), it should be understood that sensor (752) may be sized and shaped to extend adjacent to more or fewer tissue sample chambers (746). For instance, sensor (752) may be sized and shaped such that a single tissue sample (30) deposited within an individual tissue sample chamber (746) is capable of being imaged at a time. Alternatively, sensor (752) may have a greater size and shape such that multiple tissue samples (30) contained in multiple tissue sample chambers (746), respectively, may be imaged simultaneously.

Although not shown, it should be understood that tissue sample holder (730) may include multiple sensors (752) positioned below multiple tissue sample chambers (746), respectively. In this instance, sensors (752) are fixed to tissue sample chambers (746) such that rotation of tissue sample chambers (746) within tissue sample holder (730) provides for the simultaneous rotation of sensors (752). Thus, imaging device (760) may be positioned at any angle relative to tissue sample holder (730) depending on the particular tissue sample chamber (746) that an operator desires to image, rather than being required to direct imaging device (760) to the top of tissue sample holder (730) and toward the front face of sensor (752), which is securely fixed therein.

In the present example, once an operator collects one or a plurality of tissue samples (30) from a patient through biopsy device (710), imaging device (760) is selectively positioned directly above tissue sample holder (730) such that tissue sample chamber (746), containing tissue sample (30), is positioned between sensor (752) and head (762), as seen in FIG. 24. In this instance, an operator activates imaging system (750) via actuation feature (768) to transmit x-ray radiation from imaging device (760) towards tissue sample (30) until encountering sensor (752). Tissue sample (30) interacts with the radiation transmitted by head (762) and a corresponding image is generated by imaging system (750) as a result. In the present example, imaging system (750) is operable to transmit x-ray radiation from head (762) to sensor (752) to thereby generate x-ray images, however, it should be understood that imaging system (750) may be operable to generate other images using various alternative imaging modalities. By way of further example only, imaging system (750) may be operable to generate optical coherence tomography images, multipicture or videos, high definition ultrasound images, or other images as will be apparent to those of ordinary skill in the art in view of the teachings herein.

An image of tissue sample (30) is generated by imaging system (750) for the benefit of an operator's timely review and assessment. Rather than an operator detaching tissue sample holder (730) from biopsy device (710) to thereby retrieve tissue samples (30) for analysis, an operator simply rotates tissue sample chambers (746) to thereby analyze a second tissue sample (30) contained within tissue sample holder (730). In the present example, an operator is not required to initially disassemble tissue sample holder (730) from biopsy device (710), to subsequently remove tissue sample (30) from tissue sample chamber (746) for subsequent placement into an examination container (not shown) before being able to generate an image of sample (30). With sensor (752) fixedly secured within tissue sample holder (730), an operator is able to consistently align head (762) of imaging device (760) to a top portion of tissue sample holder (730) to analyze a subsequent tissue sample (30) after rotating tissue sample chambers (746) within tissue sample holder (730) such that a different tissue sample (30) is located between head (762) and sensor (752).

In this instance, an operator may extract a single tissue sample (30) from a patient and deposit the sample (30) into tissue sample chamber (746) for immediate examination by imaging device (760). Once an image of tissue sample (30) is generated, an operator may rotate tissue sample holder (730) such that an empty tissue sample chamber (746) becomes aligned with needle (711). In this instance, an operator may extract a subsequent tissue sample (30) from a patient and deposit the sample (30) into the empty tissue sample chamber (746) for subsequent examination. This method may be repeated for each tissue sample (30) extracted from a patient. Alternatively, an operator may initially extract multiple tissue samples (30) and deposit them into tissue sample chambers (746), respectively, prior to utilizing imaging device (760). In this instance, with each tissue sample chamber (746) containing an individual tissue sample (30) therein, an operator may individually image each tissue sample (30) with imaging device (460) by rotating tissue sample holder (730) to the next tissue sample chamber (746) once an image of the current tissue sample chamber (746) has been taken.

D. Imaging Device with Tissue Sample Support Arm

Figure 25:
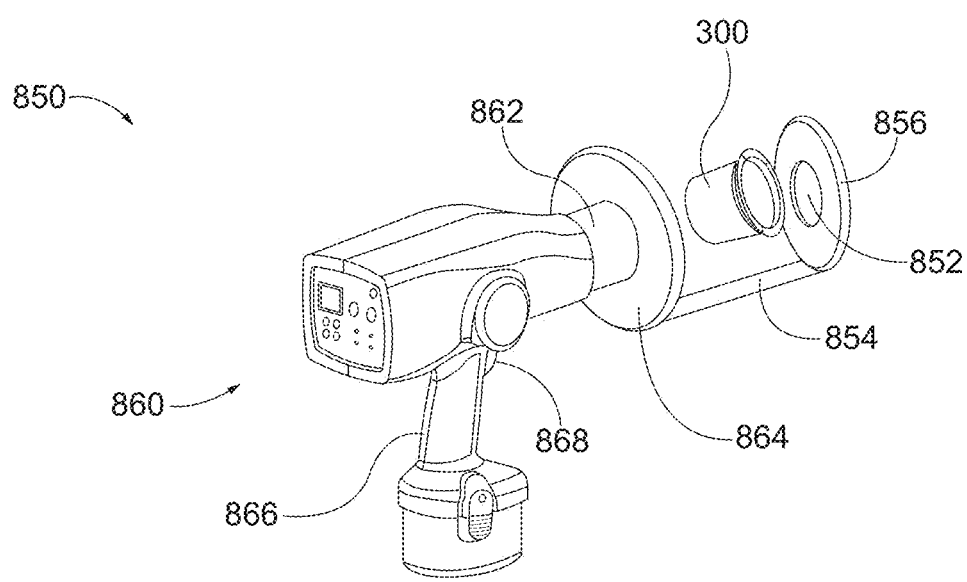
FIG. 25 depicts a perspective view of another exemplary alternative imaging device, including an exemplary clamp arm and exemplary digital sensor, with the tissue sample holder assembly of FIG. 9 received by the clamp arm.

FIG. 25 shows an exemplary imaging system (850) including an imaging device (860), an extension arm (854), and a support member (856). Except as otherwise described below, imaging system (850) and imaging device (860) may be configured and operable just like imaging system (550) and imaging device (760), respectively, described above. Imaging device (860) is a handheld device that includes a head (862), an external backscatter shield (864), a handgrip (866) and an actuation feature (868). Head (862) is configured to transmit energy or radiation outwardly upon actuation of imaging device (860) via actuation feature (868). Similar to imaging device (760), external backscatter shield (864) of imaging device (860) is positioned adjacent to, and substantially around head (862) such that head (862) is separated from a remaining portion of imaging device (860) by external backscatter shield (864).

Figure 26:
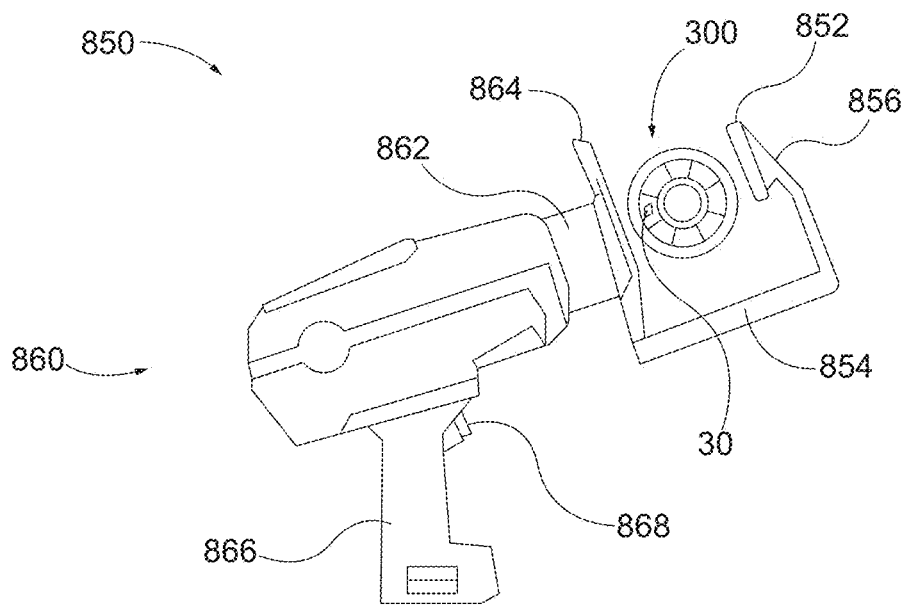
FIG. 26 depicts a side elevational view of the imaging device of FIG. 25, with the tissue sample holder assembly positioned between the digital sensor and the imaging device.

External backscatter shield (864) is operable to protect an operator from radiation exposure transmitted by head (862) when imaging device (860) is actuated. Extension arm (854) is attached to external backscatter shield (864) on a proximal end, and to support member (856) on a distal end, respectively. Extension arm (854) positions support member (856) distally from head (852) such that extension arm (854) is configured to maintain support member (856) along the direct line of sight of imaging device (860). Extension arm (854) is configured to be adjustable from an extended position, as shown in FIG. 25, to a retracted position as shown in FIG. 26. With extension arm (854) in the extended position, imaging device (860) is operable to receive tissue sample holder (300) between head (862) and support member (856). In this instance, with tissue sample holder (300) positioned therein, extension arm (854) is operable to retract support member (856) towards head (862) to thereby securely clamp tissue sample holder (300) to imaging device (860).

Support member (856) is in the form of a back plate that includes a sensor (852) integrally positioned therein. It should be understood that sensor (852) of this example may be configured and operable just like sensor (552) described above, except for the differences explicitly noted herein. Sensor (852) is centrally positioned on support member (856) and is sized and shaped to associate with the size and shape of tissue sample holder (300) such that any tissue samples (30) contained within tissue sample holder (300) are fully contained within the perimeter dimension of sensor (852). Although not shown, it should be understood that sensor (852) may be sized to an extent greater than tissue sample holder (300). Imaging device (860) is operable to communicate with sensor (852) by transmitting radiation through air until encountering sensor (852).

It should be understood that with tissue sample holder (300) positioned between sensor (852) and imaging device (860) in its entirety, imaging system (850) is operable to take an image of any tissue samples (30) contained within tissue sample holder (300). In other words, tissue sample holder (300) may contain one or more tissue samples (30) therein for imaging by imaging system (850). For instance, tissue sample holder (300) may include a single tissue sample (30), multiple tissue samples (30), or may be completely filled with numerous tissue samples (30) in every tissue sample chamber of tissue sample holder (300). Thus, imaging system (850) is operable to accurately image multiple tissue samples (30) contained within tissue sample holder (300) as the entire tissue sample holder (300) is positioned between sensor (852) and imaging device (860).

In the present example, after an operator collects a tissue sample (30) from a patient and the tissue sample (30) is deposited within tissue sample holder (300), tissue sample holder (300) is detached from biopsy device (10) and subsequently positioned within imaging device (860). Alternatively, although not shown, it should be understood that imaging system (850) may be used with tissue sample holder (300) still attached to biopsy device (10). In this instance, with tissue sample holder (300) attached to the proximal end of biopsy device (10), imaging device (860) engages the proximal end of biopsy device (10) at location of tissue sample holder (300). In either instance, tissue sample holder (300) is selectively positioned between support member (856) and head (852). With tissue sample holder (300) positioned therebetween, extension arm (864) is manipulated to thereby transition extension arm (864) from the extended position (see FIG. 25) to the retracted position (see FIG. 26). In this instance, tissue sample holder (300) is securely grasped onto imaging device (860) such that tissue sample (30) is positioned between sensor (852) and head (862), as seen in FIG. 26. An operator activates imaging system (850) via actuation feature (868) to transmit x-ray radiation from imaging device (860) towards tissue sample (30) until encountering sensor (852). Tissue sample (30) and sensor (852) interact with radiation transmitted by head (862) and a corresponding image is generated by imaging system (850) as a result.

Imaging system (850) is operable to transmit x-ray beams from head (862) to sensor (852) to thereby generate x-ray images. Alternatively, it should be understood that imaging system (850) may be operable to generate other images via various alternative imaging modalities. By way of further example only, imaging system (850) can be configured to generate optical coherence tomography, multipicture or videos, high definition ultrasound images, or other images as will be apparent to those of ordinary skill in the art in view of the teachings herein. With an image of tissue sample (30) generated by imaging system (850), an operator can review and assess the characteristics of tissue sample (30) without needing to individually remove tissue samples (30) from tissue sample holder (300) for subsequent placement into an examination container for imaging.

To examine a subsequent tissue sample (30), an operator adjusts extension arm (854) to the extended position to thereby release tissue sample holder (300) from the secured engagement with imaging system (850). An operator then removes the initial tissue sample (30) from tissue sample holder (300) and subsequently reattaches tissue sample holder (300) to biopsy device (10). In this instance, a second tissue sample (30) is extracted from the patient and deposited into tissue sample holder (300). With a new tissue sample (30) contained within tissue sample holder (300), an operator detaches tissue sample holder (300) from biopsy device (10) and selectively positions tissue sample holder (300) between head (862) and support member (856). Thus, an operator is not required to individually remove each tissue sample (30) from tissue sample holder (300) and subsequently place the sample (30) into an examination container (not shown) to generate an image of sample (30). Rather, imaging system (850) provides for the immediate imaging of tissue samples (30) contained within tissue sample holder (300).

In some instances, multiple tissue samples (30) are extracted and deposited into tissue sample holder (300) prior to imaging samples (30) with imaging device (860) such that an operator is able to examine every sample (30) contained within tissue sample (300) at once. Thus, an operator is not required to individually remove each tissue sample (30) from tissue sample holder (300) and reattach tissue sample holder (300) to biopsy device (10) to extract a subsequent specimen from the patient. Rather, an operator may initially extract multiple tissue samples (30) prior to utilizing imaging device (860). Once multiple tissue samples (30) are deposited within tissue sample holder (300), imaging device (860) may be used to image multiple tissue samples by rotating tissue sample holder (300) relative to imaging device (860) to successively align a tissue sample (30) with imaging device (860) for imaging.

Figure 27:
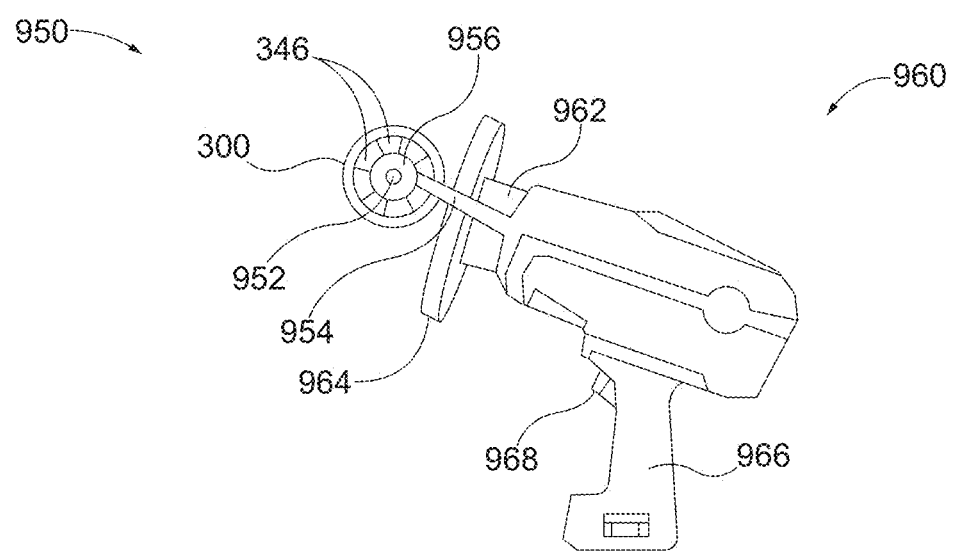
FIG. 27 depicts a side elevational view of another exemplary alternative imaging device, including an exemplary tissue holder receiving arm and exemplary digital sensor, with the tissue sample holder assembly of FIG. 9 received by the tissue holder receiving arm.

FIG. 27 shows an exemplary alternative imaging system (950) including an imaging device (960), an extension arm (954), and a support member (956). Except as otherwise described below, imaging system (950) and imaging device (960) may be configured and operable just like imaging system (550) and imaging device (760), respectively, described above. Imaging device (960) is a handheld device that includes a head (962), an external backscatter shield (964), a handgrip (966) and an actuation feature (968). Head (962) is configured to transmit energy or radiation outwardly upon actuation of imaging device (960) via actuation feature (968). Similar to imaging device (760, 860), external backscatter shield (964) of imaging device (960) is positioned adjacent to, and substantially around head (962) such that head (962) is separated from a remaining portion of imaging device (960) by external backscatter shield (964). As described above, external backscatter shield (964) is operable to protect an operator from radiation exposure transmitted by head (962) when imaging device (960) is actuated.

Figure 29:
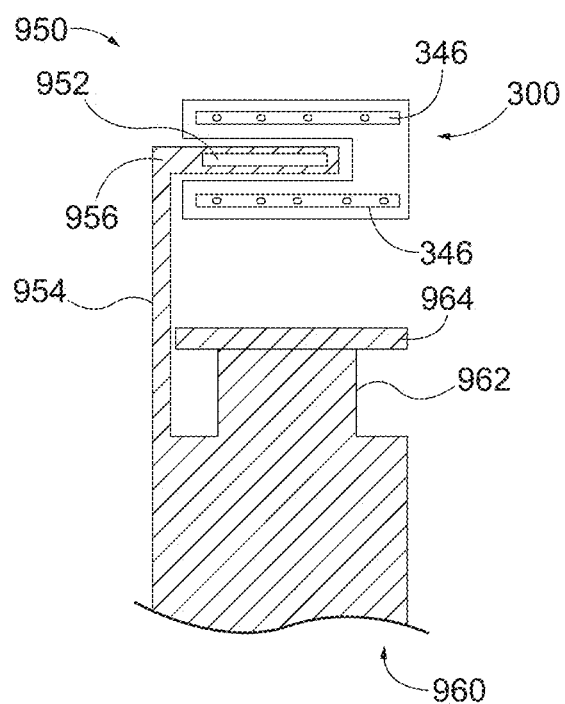
FIG. 29 depicts a partial top elevational view of the imaging device of FIG. 28, with the tissue sample holder assembly slidably engaged onto the tissue holder receiving arm.

Extension arm (954) is attached to imaging device (960) on a proximal end, and to support member (956) on a distal end, respectively. Extension arm (954) positions support member (956) distally from head (952) such that extension arm (954) is configured to maintain support member (956) along the direct line of sight of imaging device (960). Support member (956) is a revolving spindle that is sized and shaped to fit into tissue sample holder (300). In other words, support member (956) is configured to be received within tissue sample holder (300) such that tissue sample holder (300) is attachable to imaging device (960) by slidably engaging support member (956), as best seen in FIG. 29. Support member (956) includes a digital sensor (952) integrally positioned therein. It should be understood that digital sensor (952) of this example may be configured and operable just like sensor (552) described above, except for the differences explicitly noted herein. Sensor (952) is contained within support member (956) and is sized and shaped be substantially equal to, or greater than, tissue sample chamber (346) of tissue sample holder (300) such that the size of tissue sample (30) contained within tissue sample chamber (346) will not exceed beyond the dimensions of digital sensor (952) to thereby ensure a complete image of tissue sample (30) is attainable. Imaging device (960) is operable to communicate with digital sensor (952) by transmitting a radiation through air until encountering sensor (952).

Figure 28:
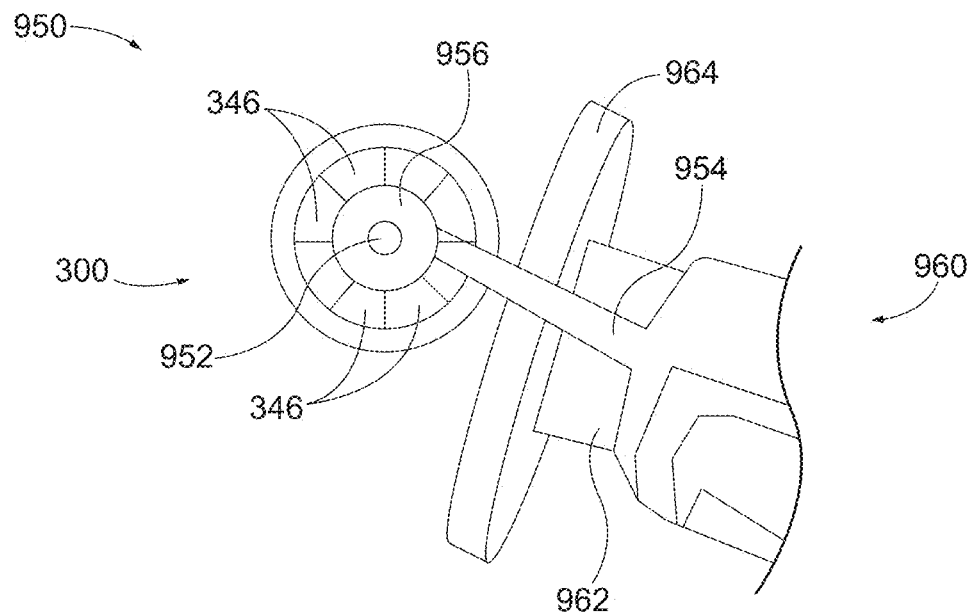
FIG. 28 depicts a partial side elevational view of the imaging device of FIG. 27, with the digital sensor contained within the tissue holder receiving arm and received through the tissue sample holder assembly.

In the present example, an operator collects tissue sample (30) from a patient with biopsy device (10) and tissue sample (30) is deposited within tissue sample holder (300). An operator then detaches tissue sample holder (300) from biopsy device (10) and subsequently attaches tissue sample holder (300) to imaging device (960). Particularly, as seen in FIG. 28, tissue sample holder (300) is slidably inserted onto support member (956). With tissue sample holder (300) engaged onto support member (956), tissue sample holder (300) is securely fastened onto imaging device (960) and positioned distally relative to head (962). An operator activates imaging system (950) via actuation feature (968) to transmit x-ray radiation from imaging device (960) towards tissue sample (30) until encountering digital sensor (952). Tissue sample (30) and sensor (952) interact with radiation transmitted by head (962) and a corresponding image is generated by imaging system (950) as a result.

In some instances, multiple tissue samples (30) are extracted and deposited into tissue sample holder (300) prior to imaging samples (30) with imaging device (960) such that an operator is able to examine every sample (30) contained within tissue sample holder (300) in a single imaging sequence. Thus, an operator is not required to individually remove each tissue sample (30) from tissue sample holder (300) and reattach tissue sample holder (300) to biopsy device (10) to extract a subsequent specimen from the patient. Rather, an operator may initially extract multiple tissue samples (30) prior to utilizing imaging device (960). In this instance, an operator rotates tissue sample holder (300) about support member (956) to realign tissue sample chambers (346) such that a different tissue sample chamber (346) is positioned in the direct line of sight with head (962) of imaging device (960).

Similar to imaging system (850) described above, imaging system (950) is operable to transmit x-ray radiation from head (962) to sensor (952) to thereby generate x-ray images. Alternatively, it should be understood that imaging system (950) may be operable to generate other images via various alternative imaging modalities. By way of example only, suitable imaging modalities may include optical coherence tomography, multipicture or videos, high definition ultrasound, or other imaging modalities as will be apparent to those of ordinary skill in the art in view of the teachings herein. With an image of tissue sample (30) generated by imaging system (950), an operator is able to review and assess the characteristics of tissue sample (30) without needing to individually remove tissue samples (30) from tissue sample holder (300) for subsequent placement into an examination container for imaging.

As discussed above, to examine a subsequent tissue sample (30), an operator rotates tissue sample holder (300) about support member (956) until an alternate tissue sample chamber (346) is positioned between head (962) and digital sensor (952). An operator then actuates imaging device (960) to thereby take an image of a different tissue sample (30) contained within the alternate tissue sample chamber (346). Alternatively, imaging system (950) may be utilized with tissue sample holder (300) still attached to biopsy device (10). Although not shown, it should be understood that in the present example support member (956) is received within tissue sample holder (300) at the proximal end opposite of the distal end that is attached to biopsy device (10). In this instance, tissue sample chambers (346) are rotated relative to biopsy device (10) such that each tissue sample (30) contained in tissue sample holder (300) is imaged by imaging device (960). In other instances, imaging device (960) is rotated about tissue sample holder (300) to thereby image each tissue sample chamber (346) that contains a tissue sample (30).

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A biopsy device, comprising: (a) a body; (b) a needle extending from the body; (c) a tissue sample holder, wherein the needle is in communication with the tissue sample holder, wherein the tissue sample holder includes a receiving cavity; and (d) a sensor, wherein the sensor is operable to digitally convert and transmit data, wherein the receiving cavity is sized and shaped to slidably receive the sensor such that the sensor is removably positioned within the tissue sample holder.

Example 2

The biopsy device of Example 1, wherein the tissue sample holder includes multiple tissue sample chambers configured to receive and hold tissue samples.

Example 3

The biopsy device of Example 1, wherein the tissue sample holder is configured to rotate relative to the body.

Example 4

The biopsy device of any one or more of Examples 1 through 3, further comprising an imaging device.

Example 5

The biopsy device of Example 4, wherein the imaging device is configured to transmit energy beams.

Example 6

The biopsy device of any one or more of Examples 2 through 5, wherein the imaging device is operable to transmit energy beams towards the tissue samples contained within the tissue sample chambers and toward the sensor.

Example 7

The biopsy device of any one or more of Examples 4 through 6, wherein the imaging device and the sensor are configured to cooperate to generate x-ray images.

Example 8

The biopsy device of any one or more of Examples 1 through 7, wherein the sensor includes an electronic circuit, an imager, a fiber optic plate and a scintillator.

Example 9

A biopsy device, comprising: (a) a body; (b) a needle extending from the body; (c) a tissue sample holder, wherein the tissue sample is configured to store tissue samples therein, and (d) at least one sensor; wherein the sensor is positioned within the tissue sample holder adjacent to the stored tissue samples, wherein the at least one sensor is operable to receive energy or radiation from an imaging device, wherein the at least one sensor is configured to digitally transmit data in response to the energy or radiation from the imaging device.

Example 10

The biopsy device of Example 9, wherein the at least one sensor is securely fixed relative to the body such that the at least one sensor maintains a static orientation during rotation of the tissue sample holder relative to the body.

Example 11

The biopsy device of Example 9, wherein the tissue sample holder includes multiple tissue sample chambers.

Example 12

The biopsy device of Example 11, wherein the tissue sample holder includes a sensor for each tissue sample chamber.

Example 13

The biopsy device of any one or more of Examples 11 through 12, wherein the sensors are securely fixed relative to the tissue sample holder such that the sensors rotate during rotation of the tissue sample holder relative to the body.

Example 14

The biopsy device of Example 13, wherein the sensor is sized and shaped to be substantially equal to a dimension of the tissue sample chamber.

Example 15

A biopsy device, comprising: (a) a body, wherein the body includes a digital sensor; (b) a needle extending from the body; (c) a tissue sample holder; and (d) a tissue sample window, wherein the tissue sample window is in communication with the needle, wherein the tissue sample window is proximate relative to the needle and distal relative to the tissue sample holder, wherein the tissue sample window includes a gate assembly configured to selectively arrest movement of a tissue sample, wherein the digital sensor is adjacent to the tissue sample window.

Example 16

The biopsy device of Example 15, wherein the tissue sample window is on a distal portion of the body.

Example 17

The biopsy device of Example 15, wherein the tissue sample window is on a proximal portion of the body.

Example 18

The biopsy device of Example 15 through Example 17, wherein the sensor is sized and shaped to be substantially equal to a dimension of the tissue sample window.

Example 19

An imaging biopsy assembly, comprising: (a) a biopsy device, wherein the biopsy device includes a body, a needle and a tissue sample holder; (b) an imaging device, wherein at least a portion of the biopsy device is configured to associate with the imaging device, wherein the at least a portion of the biopsy device is configured to maintain a tissue sample therein such that progression of the tissue sample is ceased in the at least a portion of the biopsy device, wherein the imaging device includes a beam transmitter and a sensor, wherein the beam transmitter is operable to transmit energy beams towards the sensor, wherein the sensor is operable to receive the beams, convert the received beams into data, and transmit the data.

Example 20

The imaging biopsy assembly of Example 19, wherein the imaging device includes a boom-mounted x-ray source.

Example 21

The imaging biopsy assembly of Example 19, wherein the imaging device includes a handheld x-ray source.

Example 22

The imaging biopsy assembly of Example 19 through Example 21, wherein the sensor is integral with the biopsy device.

Example 23

The imaging biopsy assembly of Example 19 through Example 21, wherein the sensor is removably separate from the biopsy device.

Example 24

A method of taking an image of a biopsied tissue sample from a biopsy device, the method comprising the steps of: (a) inserting a needle into a patient to sever and extract a tissue sample; (b) storing the tissue sample in a tissue sample holder; (c) inserting a digital sensor into the tissue sample holder such that the digital sensor is positioned adjacent to the tissue sample; (d) positioning an imaging device adjacent to the tissue sample holder such that a beam-transmitter of the imaging device is aligned towards the tissue sample and the digital sensor; and (e) activating the imaging device to transmit energy towards the tissue sample and digital sensor.

Example 25

The method of Example 24, further comprising generating an image of the tissue sample.

Example 26

The method of Example 25, further comprising displaying a graphical representation or depiction of the tissue sample.

Example 27

The method of Example 24, the method further comprising rotating the tissue sample holder to align a different tissue sample adjacent to the beam-transmitter.

Example 28

An imaging device, comprising: (a) a body, wherein the body includes a backscatter shield; (b) a beam-transmitter, wherein the beam-transmitter is operable to transmit high-energy beams; (c) an extension arm, wherein the extension arm includes a proximal end and a distal end, wherein the body and the beam-transmitter are positioned at the proximal end of the extension arm; and (d) a support member, wherein the support member is positioned at the distal end of the extension arm, wherein the support member includes a digital sensor, wherein the support member is configured to removably couple to at least a portion of a biopsy device such that the digital sensor is adjacent to at least the portion of the biopsy device.

Example 29

The imaging device of Example 28, wherein the extension arm is configured to be adjustable between an extended position and a retracted position.

Example 30

The imaging device of Example 29, wherein the support member is distally oriented relative to the body when the extension arm is in the extended position, wherein the support member is proximally oriented relative to the body when the extension arm is in the retracted position.

Example 31

The imaging device of any one or more of Examples 29 through 30, wherein at least the portion of the biopsy device is a tissue sample holder, wherein the tissue sample holder is securely engaged by the imaging device when the extension arm is in the retracted position.

Example 32

The imaging device of Example 28, wherein the backscatter shield is operable to block high-energy beams from being transmitted proximally from beam-transmitter.

Example 33

The imaging device of any one or more of Examples 30 through 31, wherein the support member is a back plate.

Example 34

The imaging device of Example 28, wherein the support member is a spindle rod.

Example 35

The imaging device of Example 34, wherein at least the portion of the biopsy device is a tissue sample holder, wherein the support member is sized and shaped to be inserted into the tissue sample holder such that the tissue sample holder is slidably received by the support member.

Example 36

The imaging device of Example 35, wherein the support member is configured to rotate the tissue sample holder about the support member.

Example 37

A biopsy device, comprising: (a) a body; (b) a needle extending from the body; (c) a tissue sample holder in communication with the needle to receive one or more tissue samples within a sample chamber defined by the tissue sample holder, wherein the tissue sample holder includes a receiving cavity; and (d) a sensor configured to detect x-rays, wherein the receiving cavity is sized and shaped to receive the sensor such that the sensor is removably positioned within the tissue sample holder.

Example 38

The biopsy device of Example 37, wherein the tissue sample holder includes a plurality of sample chambers configured to receive and hold tissue samples.

Example 39

The biopsy device of Example 37, wherein the tissue sample holder is configured to rotate relative to the body.

Example 40

The biopsy device of Example 37, wherein the tissue sample holder includes a plurality of sample chambers arranged around the receiving cavity, wherein the tissue sample holder is configured to rotate to orient the sensor relative to the plurality of sample chambers.

Example 41

The biopsy device of Example 37, further comprising an imaging device, wherein the imaging device is configured to transmit x-rays.

Example 42

The biopsy device of Example 37, further comprising an imaging device, wherein the imaging device is operable to transmit x-rays towards the tissue samples contained within the tissue sample chambers and toward the sensor.

Example 43

The biopsy device of Example 37, further comprising an imaging device, wherein the imaging device and the sensor are configured to cooperate to generate x-ray images.

Example 44

The biopsy device of Example 37, further comprising an imaging device, wherein the tissue sample holder includes a plurality of sample chambers oriented around the receiving cavity, wherein the imaging device and the sensor are configured to cooperate to generate x-ray image of each sample chamber of the plurality of sample chambers separately.

Example 45

The biopsy device of Example 37, further comprising an imaging device, wherein the tissue sample holder includes a plurality of sample chambers oriented around the receiving cavity, wherein the imaging device and the sensor are configured to cooperate to generate x-ray image of two or more sample chambers of the plurality of sample chambers in a single image.

Example 46

The biopsy device of any one or more of Examples 37 through 45, wherein the sensor includes an electronic circuit, an imager, a fiber optic plate and a scintillator.

VI. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy device with real-time imaging, comprising:
   (a) a body;
   (b) a needle extending from the body;
   (c) a tissue sample holder mounted to the body and in communication with the needle to receive one or more tissue samples, the needle and tissue sample holder together defining a sample collection path, the tissue sample holder including a plurality of tissue chambers configured to store tissue samples therein, the tissue sample holder including a receiving cavity, the receiving cavity being proximate one or more tissue chambers of the plurality of tissue chambers, the plurality of tissue chambers being arranged around the receiving cavity such that the receiving cavity is defined by a space disposed between the plurality of tissue chambers; and
   (d) a sample sensor received within the receiving cavity of the tissue sample holder adjacent to at least one tissue chamber of the plurality of tissue chambers, the sample sensor including an infrared imaging element being operable to receive radiation from a source disposed remotely with respect to the tissue sample holder, the infrared imaging element being configured to receive radiation emitted from the source and transmitted through a tissue sample disposed within any one or more of the tissue chambers.

2. The biopsy device of claim 1, the tissue sample holder being configured to rotate relative to the body.

3. The biopsy device of claim 1, the tissue sample holder including a rotatable member defining the plurality of tissue chambers, the receiving cavity of the tissue sample holder being centrally positioned relative to the plurality of tissue chambers, the receiving cavity configured to receive the sample sensor.

4. The biopsy device of claim 1, further comprising an imaging device, the imaging device being configured to transmit radiation, the imaging device and the sample sensor are configured to cooperate to generate one or more images of the one or more tissue samples.

5. The biopsy device of claim 1, further comprising a processor coupled to the sample sensor and adapted to process radiation received by the sample sensor in real-time as the biopsy of the one or more tissue samples is taking place.

6. The biopsy device of claim 1, further comprising a processor coupled to the sample sensor and a control module that controls the biopsy of the one or more tissue samples, the processor controlling a radiation source to transmit radiation through the one or more tissue samples and processing an image from the radiation received from the sample sensor in response to a signal from the control module indicating that a biopsy has been taken.

7. The biopsy device of claim 1, further comprising an imaging device, the imaging device and the sample sensor being configured to cooperate to generate image of each sample chamber of the plurality of sample chambers separately.

8. The biopsy device of claim 1, further comprising a sample window, the sample window being in communication with the needle, the sample window being disposed along the sample collection path between the needle and the tissue sample holder, the sample window including a gate assembly configured to selectively arrest movement of a tissue sample, the sample sensor being positioned proximate the sample window to receive radiation from a tissue sample of the one or more tissue samples while the tissue sample is arrested by the gate assembly.

9. The biopsy device of claim 8, the sample window being disposed on a distal portion of the body.

10. The biopsy device of claim 8, the body defining a receiving cavity disposed proximate the sample window, the receiving cavity being configured to removably receive the sample sensor.

11. The biopsy device of claim 8, the sample sensor being a reusable sensor, the body defining a receiving cavity disposed proximate the sample window, the receiving cavity being configured to removably receive the sample sensor.

12. The biopsy device of claim 8, the sample sensor being configured to receive radiation communicated through the sample window, the body defining a receiving cavity disposed proximate the sample window, the receiving cavity being configured to removably receive the sample sensor.

13. A biopsy device comprising:
(a) a body;
(b) a needle extending distally from the body;
(c) a tissue sample holder, the tissue sample holder including a plurality of tissue chambers configured to store tissue samples therein, the tissue sample holder including a receiving cavity, the receiving cavity being disposed between two or more tissue chambers of the plurality of tissue chambers; and
(d) a sensor, the receiving cavity being configured to receive the sensor along the axial length of the receiving cavity, the sensor being positioned within the receiving cavity of the tissue sample holder, the sensor being oriented within the receiving cavity towards one or more tissue chambers, the sensor being operable to receive infrared radiation from a radiation emitter, the sensor being configured to digitally transmit data in response to the radiation from the radiation emitter, the distance between the sensor and each tissue chamber being substantially the same.

14. The biopsy device of claim 13, the at least one sensor being proximate the tissue sample holder, the at least one sensor being securely fixed relative to the body such that the at least one sensor maintains a static orientation during rotation of the tissue sample holder relative to the body.

15. The biopsy device of claim 13, the tissue sample holder including a plurality of tissue chambers, the at least one sensor including a plurality of sensors with each sensor corresponding to each tissue chamber of the plurality of tissue chambers.

16. The biopsy device of claim 13, further comprising a sample window disposed proximate a distal end of the body, the at least one sensor being positioned adjacent to the sample window such that the at least one sensor is configured to receive radiation through the sample window.

17. A biopsy system, comprising:
(a) a holster;
(b) a probe configured to selectively fasten to the holster, the probe including:
(i) a probe body,
(ii) a needle extending distally from the probe body, and
(iii) a cutter adapted to move relative to the needle to sever a tissue sample;
(c) a tissue sample holder coupled to a proximal end of the probe body, the tissue sample holder being configured to receive the tissue sample, the tissue sample holder including a plurality of tissue chambers configured to store tissue samples therein and a receiving cavity oriented between at least two of the plurality of tissue chambers, the receiving cavity and the plurality of tissue chambers terminating on a common plane at the distal end of the tissue sample holder;
(d) a radiation source separate from the probe and the holster; and
(e) a sensor including an infrared imager disposed within a portion of the probe body, the sensor being positioned within the probe body or the tissue sample holder to receive radiation from the radiation source communicated through a portion of the probe body or the tissue sample holder, the sensor being equidistant from each tissue chamber; and
(f) a transmitter, the transmitter and sensor being configured to cooperate to transmit infrared through a portion of the tissue sample holder and into the receiving cavity.

18. The biopsy device of claim 17, the probe further including a sample window including a gate in communication with a portion of the cutter, the gate being configured to temporarily cease progress of the tissue sample to the tissue sample holder for inspection through the sample window, the sensor being configured to receive radiation from the radiation source communicated through the sample window.

19. The biopsy device of claim 17, the sensor including two infrared imagers used to image each sample.

20. The biopsy device of claim 17, the sensor including an electronic circuit, an imager, a fiber optic plate, and a scintillator.

* * * * *